United States Patent
Pujol Onofre et al.

(10) Patent No.: US 10,071,063 B2
(45) Date of Patent: Sep. 11, 2018

(54) SPECIFIC MTOR INHIBITORS IN THE TREATMENT OF X-LINKED ADRENOLEUKODYSTROPHY

(71) Applicants: FUNDACIÓN DE LA COMUNIDAD VALENCIANA CENTRO DE INVESTIGACIÓN PRÍNCIPE FELIPE, Valencia (ES); INSTITUT D'INVESTIGACIÓ BIOMÈDICA DE BELLVITGE (IDIBELL), Hospitalet de Llobregat, Barcelona (ES); CENTRO DE INVESTIGACIÓN BIOMÉDICA EN RED (CIBER), Madrid (ES)

(72) Inventors: Aurora Pujol Onofre, Barcelona (ES); Erwin Knecht Roberto, Valencia (ES)

(73) Assignees: FUNDACION DE LA COMUNIDAD VALENCIANA ENTRO DE INVESTIGACION PRINCIPE FELIPE, Valencia (ES); INSTITUT D'INVESTIGACIO BIOMEDICA DE BELLVITGE (IDIBELL), Barcelona (ES); CENTRO DE INVESTIGACION BIOMEDICA EN RED (CIBER), Madrid (ES); INSTITUCIO CATALANA DE RECERCA TESTUDIS AVANCATS, Barcelona (ES)

( * ) Notice: Subject to any disclaimer, the term of this patent is extended or adjusted under 35 U.S.C. 154(b) by 0 days.

(21) Appl. No.: 15/512,392

(22) PCT Filed: Sep. 21, 2015

(86) PCT No.: PCT/EP2015/071563
§ 371 (c)(1),
(2) Date: Mar. 17, 2017

(87) PCT Pub. No.: WO2016/042166
PCT Pub. Date: Mar. 24, 2016

(65) Prior Publication Data
US 2017/0273915 A1    Sep. 28, 2017

(30) Foreign Application Priority Data
Sep. 19, 2014 (EP) .................... 14382353

(51) Int. Cl.
| | | |
|---|---|---|
| A61K 31/132 | (2006.01) | |
| A61K 31/05 | (2006.01) | |
| C12Q 1/6841 | (2018.01) | |
| A61K 31/138 | (2006.01) | |
| A61K 31/194 | (2006.01) | |
| A61K 31/277 | (2006.01) | |
| A61K 31/341 | (2006.01) | |
| A61K 31/343 | (2006.01) | |
| A61K 31/436 | (2006.01) | |
| A61K 31/451 | (2006.01) | |
| A61K 31/506 | (2006.01) | |
| A61K 31/5415 | (2006.01) | |
| A61K 45/06 | (2006.01) | |
| C12Q 1/686 | (2018.01) | |

(52) U.S. Cl.
CPC ............ *A61K 31/05* (2013.01); *A61K 31/132* (2013.01); *A61K 31/138* (2013.01); *A61K 31/194* (2013.01); *A61K 31/277* (2013.01); *A61K 31/341* (2013.01); *A61K 31/343* (2013.01); *A61K 31/436* (2013.01); *A61K 31/451* (2013.01); *A61K 31/506* (2013.01); *A61K 31/5415* (2013.01); *C12Q 1/6841* (2013.01); *A61K 45/06* (2013.01); *A61K 2300/00* (2013.01); *C12Q 1/686* (2013.01)

(58) Field of Classification Search
None
See application file for complete search history.

(56) References Cited

U.S. PATENT DOCUMENTS

| | | |
|---|---|---|
| 5,262,165 A | 11/1993 | Govil et al. |
| 5,362,718 A | 11/1994 | Skotnicki et al. |
| 5,948,433 A | 9/1999 | Burton et al. |
| 6,010,715 A | 1/2000 | Wick et al. |
| 6,071,531 A | 6/2000 | Jona et al. |
| 8,029,561 B1 | 10/2011 | Kopia et al. |
| 8,258,299 B2 | 9/2012 | Lee et al. |
| 9,670,549 B2 | 6/2017 | Mock et al. |

FOREIGN PATENT DOCUMENTS

| | | |
|---|---|---|
| ES | 2303441 B1 | 6/2009 |
| ES | 2377381 B1 | 3/2013 |
| WO | 0187372 A1 | 11/2001 |

(Continued)

OTHER PUBLICATIONS

Semmler, Alexander, et al.; "Therapy of X-linked adrenoleukodystrophy," Expert Rev. Neurother., 2008, pp. 1367-1379, vol. 8.

(Continued)

Primary Examiner — Heidi L Reese
(74) Attorney, Agent, or Firm — Tristan A Fuierer; Moore & Van Allen, PLLC

(57) ABSTRACT

The invention relates to novel uses of specific mTOR inhibitors as a medicament, in particular for the treatment of X-linked adrenoleukodystrophy (X-ALD). The invention also relates to a method for identifying a compound potentially useful for the treatment and/or prevention of X-ALD.

10 Claims, 11 Drawing Sheets

(56) References Cited

FOREIGN PATENT DOCUMENTS

| WO | 2011066430 A2 | | 6/2011 | |
|---|---|---|---|---|
| WO | WO-2011066430 A2 | * | 6/2011 | ........... A61K 38/465 |
| WO | 2011144777 A1 | | 11/2011 | |
| WO | 2013071247 A1 | | 5/2013 | |

OTHER PUBLICATIONS

Fourcade, Stéphane, et al.; "Early oxidative damage underlying neurodegeneration in X-adrenoleukodystrophy," Human Molecular Genetics, 2008, pp. 1762-1773, vol. 17.

Fuertes, Graciela, et al.; "Changes in the proteolytic activities of proteasomes and lysosomes in human fibroblasts produced by serum withdrawal, amino-acid deprivation and confluent conditions," Biochem. J., 2003, pp. 75-86, vol. 375.

Galino, Jorge, et al.; "Oxidative Damage Compromises Energy Metabolism in the Axonal Degeneration Mouse Model of X-Adrenoleukodystrophy," Antioxidants & Redox Signaling, 2011, pp. 2095-2107.

Launay, Nathalie, et al.; "Oxidative stress regulates the ubiquitin-proteasome system and immunoproteasome functional in a mouse model of X-adrenleukodystrophy," BRAIN A Journal of Neurology, 2013, pp. 891-904, vol. 136.

López-Erauskin, Jone, et al.; "Antioxidants Hault Axonal Degeneration in a Mouse Model of X-Adrenoleukodystrophy," Ann Neurol, 2011, pp. 84-92, vol. 70.

International Search Report, dated Nov. 5, 2015.

\* cited by examiner

A

B dystrophy (X-ALD). The invention
SPECIFIC MTOR INHIBITORS IN THE TREATMENT OF X-LINKED ADRENOLEUKODYSTROPHY

CROSS-REFERENCE TO RELATED APPLICATIONS

This application is filed under the provisions of 35 U.S.C. § 371 and claims the priority of International Patent Application No. PCT/EP2015/071563 filed on 21 Sep. 2015 entitled "SPECIFIC MTOR INHIBITORS IN THE TREATMENT OF X-LINKED ADRENOLEUKODYSTROPHY" in the name of Aurora PUJOL ONOFRE, et al., which claims priority to European Patent Application No. 14382353.2, filed on 19 Sep. 2014, both of which are hereby incorporated by reference herein in their entirety.

FIELD OF THE INVENTION

The invention relates to novel uses of specific mTOR inhibitors as a medicament, in particular for the treatment of X-linked adrenoleukodystrophy (X-ALD). The invention also relates to a method for identifying a compound potentially useful for the treatment and/or prevention of X-ALD.

BACKGROUND OF THE INVENTION

X-linked adrenoleukodystrophy (X-ALD) is a neurometabolic disease characterized by the accumulation of very-long chain fatty acids (VLCFA) due to the loss of function of the peroxisomal transporter ABDC1. The X-ALD is the most common demyelinizating disease, monogenic inherited with a minimum incidence of 1:17,000 males. Clinically, X-ALD is characterized by a progressive damage to the brain, adrenal gland, peripheral nervous system and eventually death.

X-ALD shows three main phenotypes, an adult adrenomyeloneuropahy (AMN) with axonopathy in spinal cords, a cerebral adrenomyeloneuropathy with brain demyelinization (cAMN) and a childhood variant characterized by severe cerebral demyelinization. Some dietary treatments, for example, Lorenzo's oil, a mixture of glyceryl trioleate and glyceryl trierucate in combination with a diet low in very long chain saturated fatty acids have been used with limited success in the treatment of X-ALD since the levels of VLCFA does not decrease in brain tissues.

The treatment of X-ALD by means of allogenic bone marrow transplantation has been successful when the transplantation is done before getting the disease onset. However, said treatment has several limitations because it can only be done when there is available HLA-matched donor and carries an elevated risk of mortality.

Another therapeutic strategy is based on the use of the histone deacetylase (HDAC) inhibitors 4-phenylbutyrate and valproic acid (ES2303441-B1).

The use of a combination of N-acetylcysteine and alpha lipoic acid has been disclosed as antioxidant therapy for treatment of X-ALD. Said treatment is effective in correcting oxidative damage due to the excess of VLCA. Nevertheless, the exacerbation of oxidative stress in X-ALD, although is associated with the cell damage during the disease progression, is not the cause of the development of the X-ALD itself (ES2377381-B1).

In view of the above, there is a need of new therapies for the treatment of X-ALD directed to molecular targets that trigger said pathology.

BRIEF SUMMARY OF THE INVENTION

In a first aspect, the invention relates to a specific mTOR inhibitor for use in the treatment and/or prevention of X-Adrenoleukodystrophy (X-ALD) in a subject.

In a second aspect, the invention relates to a composition comprising a specific mTOR inhibitor and a compound selected from the group consisting of an mTOR-independent autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hipolipidemic drug.

In a third aspect, the invention relates to the composition defined in the second aspect of the invention for use in medicine.

In a forth aspect, the invention relates to the composition defined in the second aspect of the invention for use in the treatment and/or prevention of X-Adrenoleukodystrophy (X-ALD) in a subject.

In a fifth aspect, the invention relates to a pharmaceutical composition comprising the composition defined in the third aspect of the invention and a pharmaceutically acceptable excipient.

In a sixth aspect, the invention relates to a method for identifying a compound potentially useful for the treatment and/or prevention of X-ALD comprising:
a) contacting an X-ALD cell with the candidate compound; and
b) assaying a marker in the presence of said candidate compound, wherein the marker is selected from the group consisting of:
(i) mTOR activity levels and
(ii) the expression level of an autophagosome marker;
wherein if said candidate compound inhibits the activity of mTOR and/or alters the expression of the autophagosome marker, then the candidate compound is useful for the treatment and/or prevention of X-ALD.

DETAILED DESCRIPTION OF THE INVENTION

Figure 1:
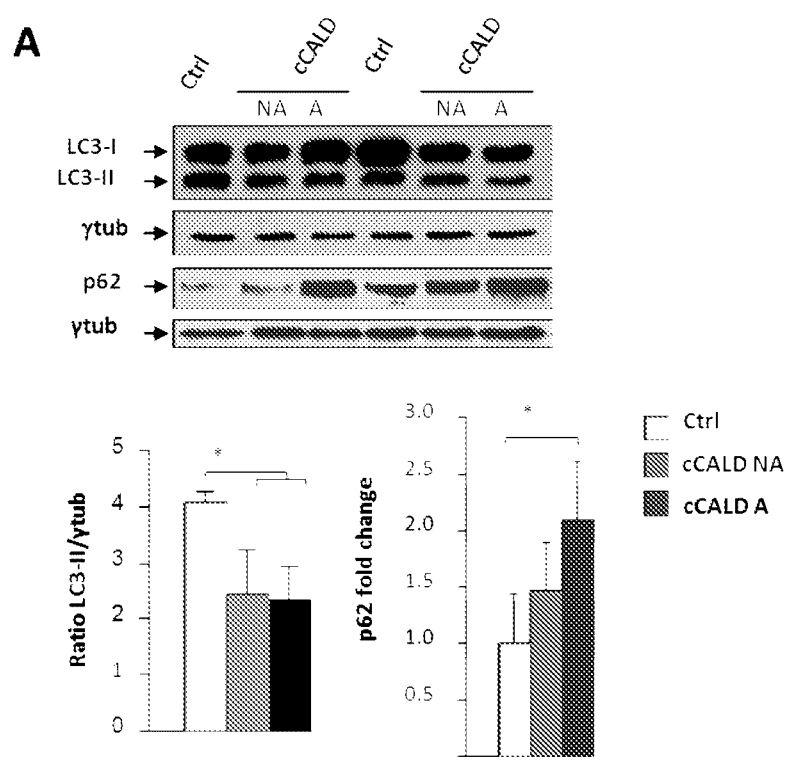
FIG. 1: Immunoblot analysis of p62 and LC3-II levels in control individuals (Ctrl) and in non-affected (NA) and affected (A) brain areas of cCALD (A) and cAMN (B) patients, and in spinal cords of wild type (WT) and Abcd1−/− mice (C) at 3 and 12 months. The position of the LC3-I and LC3-II bands are indicated on the left of the LC3 Western blots and γ-tubulin (γtub) was used as a loading control. The histograms show the quantification of LC3-II bands referred to the γtub levels and the p62 levels relative to the respective controls. LC3-II protein levels were down-regulated, whereas increased p62 levels were detected in all X-ALD models. Data represent the mean±SD of 4-5 (A and B) and 6 (C) independent experiments. *p<0.05 and **p<0.01.
Figure 1:
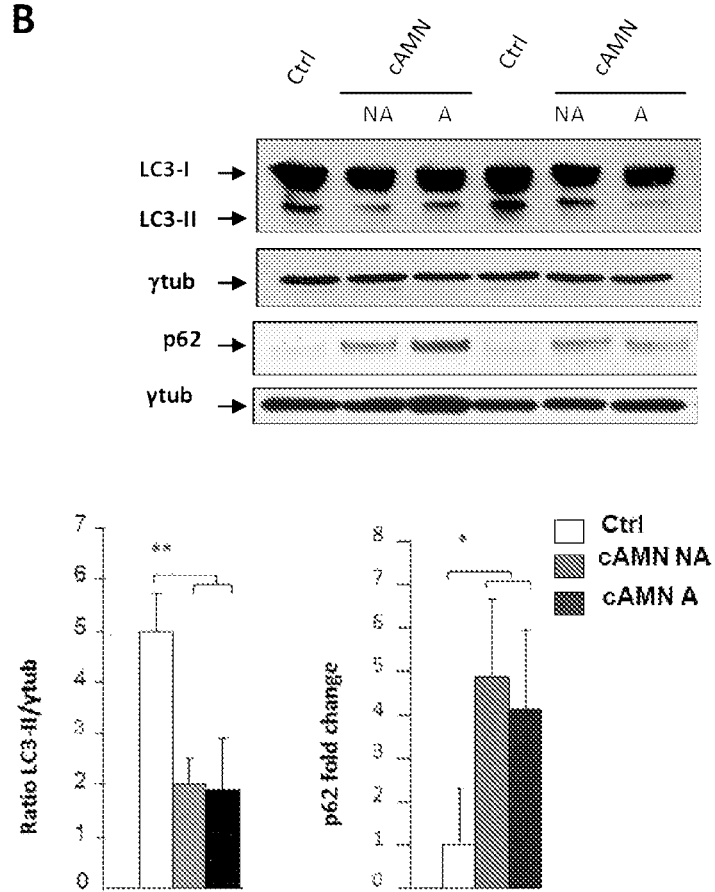
Figure 1:
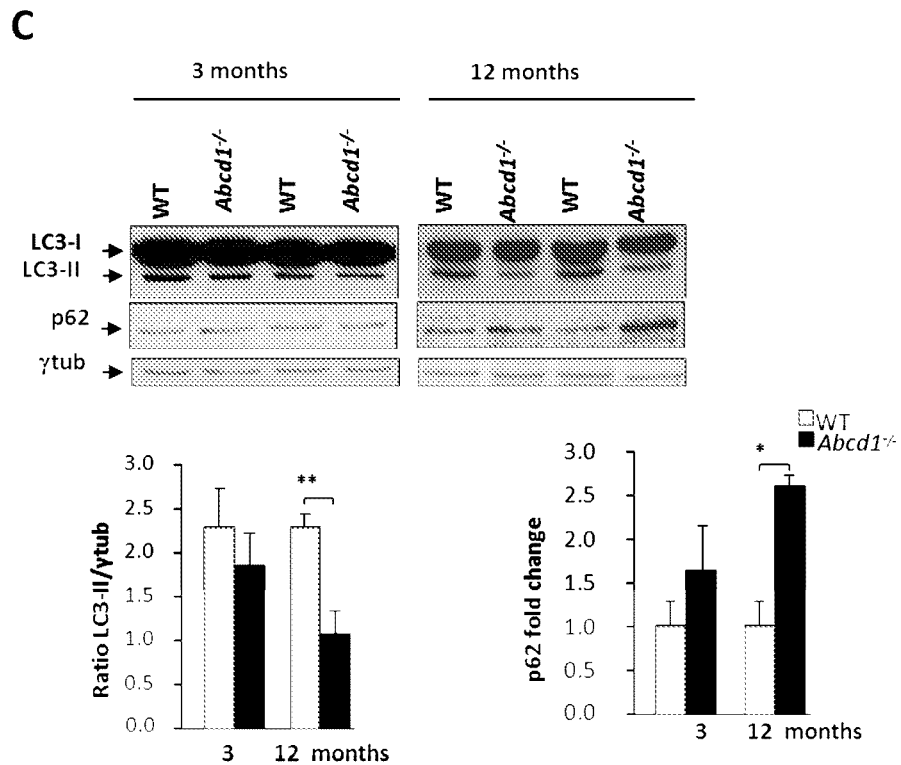

The authors of the present invention have found that, surprisingly, an aberrant mTOR signalling causing an impairment of autophagy is a mechanistic component of the pathogenesis of X-ALD and that the symptoms of X-ALD can be corrected in a mouse X-ALD model by the administration of an mTOR inhibitor.

Medical Use of a Specific mTOR Inhibitor

In the first aspect, the invention relates to a specific mTOR inhibitor for use in the treatment and/or prevention of X-Adrenoleukodystrophy (X-ALD) in a subject.

The term "mTOR" as used herein refers to the mammalian target of rapamycin, also known as FK506-binding protein or 12-rapamycin-associated protein 1. mTOR is a serine/threonine protein kinase that regulates cell growth, cell proliferation, cell motility, cell survival, protein synthesis and transcription. Human mTOR is encoded by the mTOR gene (accession number NM_004958 according to the NCBI database as of 25 May 2014). mTOR functions as the core catalytic component of two structurally and functionally distinct complexes, mTOR complex 1 (mTORC1) and mTOR complex 2 (mTORC2). In a preferred embodiment, the term "mTOR" according to the invention means the mTOR protein which is integrated in the mTORC1 complex. The mTORC1 complex is composed of mTOR, regulatory-associated protein of mTOR or Raptor, the mammalian lethal with SEC13 protein 8 (MLST8), the PRAS40 protein and the DEPTOR protein. When mTOR activity is suppressed either through growth factor signalling inhibitors or nutrient withdrawal, autophagy is induced. On the contrary, positive regulation of mTOR inhibits autophagy.

The term "specific mTOR inhibitor" as used herein, refers to a compound with high specificity for its target (e.g. mTOR). Specificity of a particular inhibitor is defined as a ratio of the IC50 values of the particular inhibitor for the target of interest versus another target. For example, a specific mTOR inhibitor will have an IC50 value for mTOR lower than that for other targets. For example, the IC50 value for mTOR is at least 10 times lower than the IC50 value of the same inhibitor for other targets. In other examples, the IC50 value for mTOR is 100 times lower, or in other example is 1000 times lower. In still other example, the IC50 value for mTOR is 10,000 times lower than the IC50 value of the same inhibitor for other target.

A specific mTOR inhibitor according to the present invention includes compounds which prevent the expression of mTOR gene, compounds which lead to reduced mTOR mRNA or protein levels, as well as any compounds that inhibit the activity of mTOR.

The term "activity of mTOR" as used herein, refers to cellular transduction signals regulated by mTOR that are involved in several cellular processes such as protein synthesis, cell motility, survival, autophagy and metabolism in response to hormones, growth factors and nutrients. In a preferred embodiment, a specific mTOR inhibitor refers to a compound or ligand, or a pharmaceutically acceptable salt thereof that inhibits the mTOR suppression of autophagy, that is to say, which activates autophagy.

The term "pharmaceutically acceptable salt" as used herein, refers to salts that retain the biological effectiveness of the free acids and bases of the specified compound and that are not biologically or otherwise undesirable. Examples of pharmaceutically acceptable salts include those salts prepared by reaction of the compounds described herein with a mineral or organic acid such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

The term "autophagy", as used herein, refers to a catabolic cell mechanism that involves cell degradation of unnecessary or dysfunctional cellular components such as intracellular proteins, protein aggregates, cellular organelles, cell membranes, organelle membranes and other cellular components through the actions of lysosomes. The mechanism of autophagy may include: (i) the formation of a membrane around a targeted region of the cell, separating the contents from the rest of cytoplasm, (ii) the fusion of the resultant vesicle with a lysosome or an endosome and the subsequent degradation of the vesicle contents. The term autophagy may also refer to one of the mechanisms by which a starving cell reallocates nutrients from less necessary to more essential processes.

In one embodiment, the specific mTOR inhibitor is a compound which leads to a reduction in the protein or mRNA levels of mTOR.

In a particular embodiment, the mTOR specific inhibitor is a mTOR-specific inhibitory antibody. The term "inhibitory antibody", as used herein, relates to an antibody which specifically binds to mTOR and is capable of inhibiting at least partially the biological activity of mTOR. Methods for the obtention of antibodies are known by the skilled in the art. The antibodies to be employed in these methods can be, for example, polyclonal sera, hybridoma supernatants or monoclonal antibodies, antibody fragments, Fv, Fab, Fab' and F(ab')2, ScFv, diabodies, triabodies, tetrabodies and humanized antibodies.

In a particular embodiment, the specific mTOR inhibitor for use according to the invention is a mTOR-specific RNA interference (RNAi), which is capable of knocking down the expression of mTOR or of any gene necessary for mTOR function. In the context of the invention, the RNAi specific for mTOR may be comprised by a stable viral vector system, such as an adenovirus.

In a particular embodiment, the specific mTOR inhibitor for use according to the invention is a mTOR-specific short-interfering RNA (siRNA).

In a particular embodiment, the specific mTOR inhibitor for use according to the invention is a mTOR-specific microRNA. MicroRNAs are enzymatic RNA molecules capable of catalyzing the specific cleavage of RNA. The mechanism of microRNA action involves sequence specific hybridization of the microRNA molecule to complementary target RNA, followed by an endonucleolytic cleavage event. The composition of microRNA molecules preferably includes one or more sequences complementary to a target mRNA, and the well-known catalytic sequence responsible for mRNA cleavage or a functionally equivalent sequence.

In a particular embodiment, the specific mTOR inhibitor for use according to the invention is a mTOR-specific antisense nucleic acid, which inhibits transcription and/or translation of mTOR nucleic acid. mTOR inhibiting antisense nucleic acids according to the invention include, without limitation, human mTOR antisense compounds as disclosed.

In a particular embodiment, the specific mTOR inhibitor for use according to the invention is a mTOR-specific DNA enzyme. DNA enzymes incorporate some of the mechanistic features of both antisense and microRNA technologies. DNA enzymes are designed so that they recognize a particular target nucleic acid sequence, much like an antisense oligonucleotide, however much like a microRNA they are catalytic and specifically cleave the target nucleic acid.

The expression of a protein or nucleic acid is considered reduced when its levels decrease with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent).

The reference value refers to the level of a mRNA or protein in control subject, which may be a subject who does not suffer a specific disease. In the context of the present invention, the reference value refers to the protein or mRNA level of mTOR in a control subject, thus, a subject who does not suffer X-ALD. The reference value also includes the expression level of mTOR (i.e. mRNA or protein levels) in a control subject.

Suitable methods for determining whether an inhibitor specific for mTOR is capable of decreasing mTOR mRNA levels include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE), including variants such as LongSAGE and SuperSAGE, microarrays, fluorescence in situ hybridization (FISH), including variants such as Flow-FISH, qFiSH and double fusion FISH (D-FISH), and the like.

Suitable methods for determining whether an inhibitor acts by decreasing the mTOR protein levels include the quantification by means of conventional methods, for example, using antibodies with a capacity to specifically bind to the proteins encoded by mTOR gene (or to fragments thereof containing antigenic determinants) and subsequent quantification of the resulting antibody-antigen complexes. There are a wide variety of well-known assays that can be used in the present invention, which use non-labeled antibodies (primary antibody) and labeled antibodies (secondary antibodies); among these techniques are included Western blot or Western transfer, ELISA (enzyme linked immunosorbent assay), RIA (radioimmunoassay), competitive EIA (enzymatic immunoassay), DAS-ELISA (double antibody sandwich ELISA), immunocytochemical and immunohistochemical techniques, techniques based on the use of biochips or protein microarrays including specific antibodies or assays based on colloidal precipitation in formats such as dipsticks. Other ways of detecting and quantifying the levels of the protein of interest include techniques of affinity chromatography, binding-ligand assays, etc.

In another embodiment, the specific mTOR inhibitor acts by inhibiting mTOR activity. A specific mTOR inhibitor for use in the present invention may specifically inhibit mTOR activity by at least 5%, at least 10%, at least 25%, at least 50%, at least 75%, or at least 90%, and all ranges between 5% and 100%. Suitable methods for determining whether an inhibitor acts by decreasing the mTOR activity include any method which allows the determination of mTOR activity levels such as by determining the phosphorylation level of any substrates which are phosphorylated by mTOR such as p70S6K, EIF4EBP1 and ULK1 proteins. Assays to determine the activity of an enzyme are known by the skilled person and include, without limitation, initial rate assays, progress curve assays, transient kinetics assays and relaxation assays. Continuous assays of enzymatic activity include, without limitation, spectrophotometric, fluorometric, calorimetric, chemiluminescent, light scattering and microscale thermopheresis assays. Discontinuous assays of enzymatic activity include, without limitation, radiometric and chromatographic assays. As the skilled person understands, factors that may influence enzymatic activity comprise salt concentration, temperature, pH, and substrate concentration.

The term "EIF4EBP1", as used herein, refers to the eukaryotic translation initiation factor 4E-binding protein as shown in the Uniprot database under accession number Q13541 at date 11 Jun. 2014. EIF4BP1 regulates eIF4E activity by preventing its assembly into the eIF4F complex. The phosphorylated form of EIF4EBP1 is regulated by mTOR, in the context of the mTORC1 complex, and actives translation.

The term "P-p70S6K" or "phosphorylated p70S6K" as used herein, refers to the phosphorylated form of the 70 kDa serine/threonine protein S6 kinase as shown in the Uniprot database under accession number P23433 at date 14 May 2014. It acts downstream of PPI3 and phosphoinositide-dependent kinase-1 in the PI3 kinase pathway. Its target substrate is the S6 ribosomal protein. Phosphorylation of S6 induces protein synthesis at the ribosome. p70S6K is phosphorylated by mTOR, which leads the formation of the activated form of the protein, P-p70S6K, and acts downstream of mTOR signaling in response to growth factors and nutrients to promote cell proliferation and cell cycle progression.

The term "ULK1" as used herein, refers to the eukaryotic serine/threonine kinase as shown in the Uniprot database under accession number 075385 at date 9 Jul. 2014. It acts upstream of phosphatidylinositol 3-kinase PIK3C3 to regulate the formation of phagophores. Said protein is phosphorylated by mTOR.

In preferred embodiments of the invention, the determination of the inhibitory capacity on the biological activity of mTOR can be detected by in vitro assays based on measurement of expression levels of p70S6 kinase or other mTOR substrates in their phosphorylated forms (P-p70S6, P-EIF4EBP1, P-ULK1). There are multiple assays known in the state of the art which allow the determination of the phosphorylated form of a protein. Said methods include kinase activity assays based on the measurement of the phosphorylated substrate (e.g. phosphorylated p70S6) in presence of the specific kinase (i.e. mTOR), the substrate of the kinase (i.e. p70S6) and ATP. Generally, the detection of the phosphorylated substrate is carried out by several reporter systems including colorimetric, radioactive or fluorimetric detection. Other assays which allow the detection of phosphorylated proteins include, but are not limited to, suitable methods for determining protein levels such Western blot, ELISA, Flow cytometry, immunocytochemistry, immunohistochemistry and mass spectrometry.

Alternatively, the measurement of a phosphorylated protein can be carried out by using phospho-specific antibodies which specifically recognize the phospho-protein of interest. When using this technique, it is recommendable normalizing the level of the phospho-protein to total level of said protein. For example, when determining the activity of mTOR by measuring the level of the P-p70S6 protein, the results are normalized by determining the level of the p70S6 protein.

The activity of mTOR is considered reduced if the levels of the substrates which are phosphorylated by mTOR (p70S6K, EIF4EBP1 or ULK1) are decreased with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., undetectable).

Alternatively, the determination of the inhibitory capacity on the biological activity of mTOR can be detected by in vitro assays based on measurement of the expression levels of markers which are related to the cellular processes regulated by mTOR such as autophagy.

Thus, in a preferred embodiment of the present invention, suitable methods for determining whether a specific mTOR inhibitor is capable of decreasing mTOR activity comprises determining the expression level of at least one autophagosome marker. The term "autophagosome marker" or "autophagic marker" as used herein, refers to proteins or their encoding genes, which are differentially expressed in autophagy. Illustrative examples of autophagosome markers, which are useful for determining the activity of mTOR according to the first aspect of the invention, include, but are not limited to LC3-II and p62. In a preferred embodiment, the expression level of said autophagy markers is determined under basal autophagic conditions. The expression "basal autophagic conditions", as used herein, refers to said conditions in which constitutively autophagy occurs in low levels as part of cellular mechanisms involved in constitutive turnover of cytosolic components; thus basal autophagic conditions allow cell growth. In another preferred embodiment, the expression level of said autophagic markers is determined under conditions which stimulate autophagy. The expression "conditions which stimulate autophagy" as used herein, refers to conditions which induce the degradation of the cells by autophagy. Conditions which stimulate autophagy include nutrient starvation, hormone treatment and stress. The most typical trigger of autophagy is nutrient starvation. Hormones and growth factors deprivation also seem to contribute to autophagy induction in many cell types. Typically, conditions for inducing autophagy in cell cultures comprise growing cells either in nutrients or serum deprivation media.

The term "LC3-II" as used herein, refers to the Autophagy-related protein LC3 or microtubule-associated proteins 1A/1B, as shown in the Uniprot database under accession number Q9H492 at date 14 May 2014. It is involved in formation of autophagosomal vacuoles. LC3-II is obtained by lipidation of the LC3-I protein.

The term as used herein, refers to phosphotyrosine-independent ligand for the Lck SH2 domain of 62 kDa ubiquitin-binding protein p62, also known as Sequestosome 1, as shown in the Uniprot database under accession number Q13501 at date 14 May 2014. It is required both for the formation and autophagic degradation of polyubiquitin-containing bodies.

The activity of mTOR is considered reduced when the levels of one or more of the autophagosome markers (e.g. p62) are decreased with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., undetectable). Additionally, the activity of mTOR is considered reduced when the levels of one or more autophagosome markers (e.g. LC3-II) are increased with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%.

Illustratively, the determination of the inhibitory capacity of a specific mTOR inhibitor according to the present invention can be carried out as it is demonstrated in example 6 of the present patent application by determining the activation of the autophagic flux in treated cells with a specific inhibitor of mTOR. Cells obtained from X-ALD patients which are treated with a specific inhibitor of mTOR show reduced levels of the P-p70S6K and p62 proteins when compared with the said proteins level determined in cells obtained from X-ALD patients which are not being treated with said inhibitor. Moreover, cells obtained from patient suffering from X-ALD show an increase in the level of the LC3-II protein when compared with the level of said marker in cells obtained from said patients which are not being treated.

The person skilled in the art understands that expression levels of said autophagosome markers can be determined by means of determining the mRNA level or the protein level thereof. Suitable methods for determining mRNA level or protein level have been detailed above. In a preferred embodiment, the expression level of said markers is determined by means of determining their protein levels. Suitable methods for determining the protein level of a specific marker have been previously detailed. In a still more preferred embodiment of the invention, the protein level of said autophagosome markers is determined by Western blot.

The oxidative stress mechanism contributes to the progression of X-ALD. Signs of oxidative stress in spinal cords of patients suffering from X-ALD include oxidative, glycoxidative and lipoxidative damage to proteins and altered enzymatic antioxidant defense. The authors of the present invention have demonstrated that cells obtained from X-ALD patients show reduced level of oxidized proteins under treatment with a specific mTOR inhibitor. Thus, in a preferred embodiment of the invention, the determination of whether a specific mTOR inhibitor is capable of decreasing mTOR activity, further comprises determining the expression level at least one oxidative damage marker. The term "oxidative damage marker" refers to any marker such as proteins or their encoding genes, which is differentially expressed during the oxidative stress process. The term "oxidative stress process", as used herein, refers to the imbalance between the systemic manifestation of reactive oxygen species and a biological system's ability to readily detoxify the reactive intermediates or to repair the resulting damage. Illustrative examples of oxidative markers which can be used to determine the activity of mTOR according to this aspect of the invention include but are not limited to the expression levels of oxidized proteins, the expression levels of the immunoproteasome subunits β1i/LMP2 and β5i/LMP7, the chymotrypsin-like activity of proteasomes and the ATP levels.

The term "oxidized proteins", as used herein, refers to the covalent modification of a protein induced either directly by reactive oxygen species or indirectly by reaction with secondary products of oxidative stress. The most common products of protein oxidation in biological samples are the protein carbonyl derivatives of Pro, Arg, Lys and Thr. These derivatives are chemically stable and serve as markers of oxidative stress for most types of reactive oxygen species. Suitable methods for determining oxidized proteins are based on the detection of chemically modifications such disulphides, thyil radicals, glutathiolation, methionine sulfoxide groups, carbonyls groups etc. Said methods include but are not limited to SDS-gel electrophoresis in absence of β-mercaptoethanol, electro-spin resonance spectroscopy detection, mass spectroscopy, cyanogen bromide cleavage followed by aminoacid analysis, dinitrophenylhydrazyne-coupled assay, Western blot, ELISA, immunoassays etc.

The term "β1i/LMP2" or "immunoproteasome subunit LMP2" as used herein, refers to the protein as shown in the Uniprot database under accession number P28065 at date 14 May 2014. The term "β5i/LMP7" or "immunoproteasome subunit LMP7" as used herein, refers to the protein as shown in the Uniprot database under accession number P28062 at date 14 May 2014. The expression level of β1i/LMP2 and/or β5i/LMP7 can be determined by any suitable method known in the art which allow the determination of the protein level or the mRNA levels.

The term "chymotrypsin-like activity of the proteasome" as used herein, refers the proteolytic activity of the proteasome which is regulated by the subunit β5 of the proteasome. Methods for determining chymotrypsin-like activity of proteasomes are known by the person skilled in the art which include colorimetric, luminometric and fluorometric assays. Illustratively, the determination of the chymotrypsin-like activity of the proteasome can be assayed by incubating a proteasome extract with a specific substrate for the chymiotrypsin like proteases such the Suc-LLVY substrate, which is preferably modified with a fluorigenic tag, such as AMC. The proteolytic activity is then determined by the measurement of the free AMC fluorescence by using a fluorescence reader The term "ATP" or "adenosine triphosphate" as used herein, refers to the adenosine nucleoside triphosphate which is used in cells as a coenzyme. ATP transports chemical energy within cells for metabolism. Methods for determining ATP levels are known by the person skilled in the art which include colorimetric, luminometric and fluorometric assays. Commercial kits useful for determining ATP levels include ATPlite 1 step from PerkinElmer which is based in the production of light caused by the reaction of ATP with added luciferase and D-luciferin.

The activity of mTOR is considered reduced when the levels of one or more of the markers of oxidative damage (e.g. oxidized proteins, β1i/LMP2 or ATP) are decreased with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., undetectable).

Example 7 of the application shows the effect of a specific mTOR inhibitor on the levels of oxidative damage markers. Cells obtained from X-ALD patients treated with a specific mTOR inhibitor show lower levels of oxidized proteins than cells obtained from X-ALD patients that are not under said treatment. Said treatment also prevents the bioenergetic failure associated with oxidative stress normalizing ATP levels in cells obtained from X-ALD patients and prevents the induction of the chymotrypsin-like activity of proteasomes and the levels of immunoproteasome subunits β1i/LMP2 and β5i/LMP7.

The authors of the present invention have also demonstrated that axonal degeneration, which is associated with X-ALD development, is prevented by the treatment with a specific mTOR inhibitor. Thus, in another preferred embodiment of the invention, suitable methods for determining whether a specific mTOR inhibitor is capable of decreasing mTOR activity further comprises determining the expression level of at least one axonal damage marker. The term "axonal damage marker", as used herein, refers to proteins or their encoding genes which are differentially expressed in axonal damage. The term "axonal damage", as used herein, refers to axonal injury which implies demyelinating process. Illustrative markers of axonal damage which can be used include but are not limited to Iba-1, GFAP, synapthoysin, APP and 8-oxo-7,8-dihydro-2'-deoxyguanosine.

The term "Iba-1" or "AIF-1", as used herein, refers to the ionized calcium-binding adapter molecule 1 or allograft inflammatory factor 1, as shown in the Uniprot database under the accession number P55008 at date 14 May 2014.

The term "GFAP", as used herein, refers to the glial fibrillary acidic protein as shown in the Uniprot database under the accession number P14136 at date 14 May 2014.

The term "synaptophysin" or "major synaptic vesicle protein p38", as used herein, refers to the protein as shown in the Uniprot database under the accession number P08247 at date 14 May 2014.

The term "APP" or "Amyloid beta A4 protein", as used herein, refers to the protein as shown in the Uniprot database under the accession number P05067 at date 14 May 2014.

The term "8-oxo-7,8-dihydro-2'-deoxyguanosine" or "8-oxodG", as used herein, refers to a oxidized purine nucleoside. Said marker is indicative of DNA lesions.

The activity of mTOR is considered reduced of the levels of one or more of the markers of axonal damage (e.g. Iba-1, GFAP, synaptophysin, APP or 8-oxo-7,8-dihydro-2'-deoxyguanosine) are decreased with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., undetectable). In a particular embodiment, said specific mTOR inhibitor is a rapamycin-derivative.

The term "rapamycin-derivative", as used herein, refers to a chemically modified rapamycin. Rapamycin is a macrolitic triene antibiotic produced by *Streptomyces hygroscopicus*. Said rapamycin-derivatives compounds include but are not limited to temsirolimus, deforolimus, (Ridaforolimus, AP23573 and MK-8669), Everolimus (RAD001), AZD8055, OSI-027, BEZ235 (NVP-BEZ235), INK-128, XL388, P2281, P529, GSK2126458, KU-0063794, WAY-001, WAY-600, WYE-687, Wyeth-BMCL-2000910075-9b, Wyeth-BMCL-200910096-27, KU-BMCL-200908069-5, KU-BMCL-200908069-I, PI-103, WYE-354, Torin1, PP242, PP30, PP487, PP121 and XL765 rapamycin 16-O substituted rapamycin, 40-O substituted rapamycin, mono- and di-ester derivatives of rapamycin, 27-oximes of rapamycin, 42-oxo analog of rapamycin, bicyclic rapamycin, rapamycin dimers, silyl ethers of rapamycin and rapamycin arilsulfonates and sulfamates.

In a still more particular and a preferred embodiment, said specific mTOR inhibitor is temsirolimus.

The term "temsirolimus" as used herein refers to a hydroxyl ester at the 42$^{nd}$ position of rapamycin. Chemical name of temsirolimus is (3S,6R,7E,9R,10R,12R, 14S,15E, 17E,19E,21S,23S,26R,27R,34aS)-9,10,12,13,14,21,22,23, 24,25,26,27,32,33,34,34a-Hexa deca hydro-9,27-dihydroxy-3-[(1R)-2-[1S,3R,4R)-4-hydroxy-3-methoxy cyclohexyl]-10,21-dimethoxy-6,8,12,14,20,26-hexa meth 3H-pyrido [2,1-][1,4]oxa azaclo hentriacontine-1,5,11,28,29 (4H,6H,31H)-pentone 4'-[2,2-bis (hydroxymethyl)propionate]; or Rapamycin, 43-[3-hydroxy-2-(hydroxymethyl)-2-methylpropanoate]. This compound is widely used in treatment of renal carcinoma. The term temsirolimus also encompasses a prodrug, derivative or analog thereof. The chemical structure of temsirolimus is represented by:

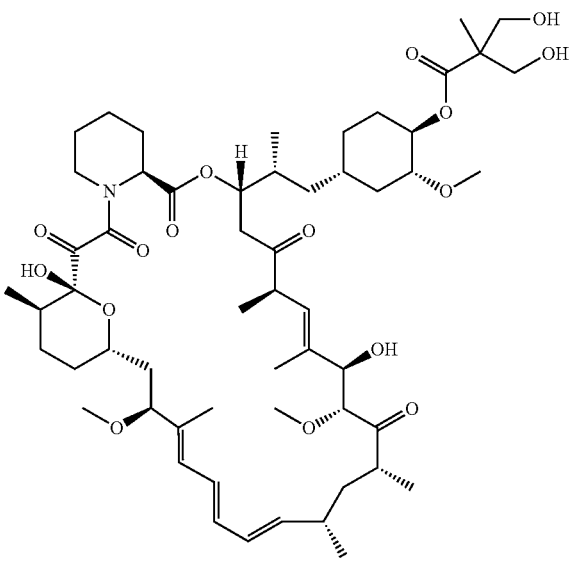 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C(C)(CO)CO)[C@H](OC)C2)CC(=O)[C@H](C)/C=C(\C)[C@@H](O)[C@@H](OC)C(=O)[C@H](C)C[C@H](C)/C=C/C=C/C=C/1C]

Temsirolimus is a compound that can be obtained by the skilled person by methods known in the art including, without limitation, those described in U.S. Pat. No. 85,362,718 B1 or U.S. Pat. No. 8,258,299 B2. Temsirolimus is also commercially available from Pfizer (Torise®).

The term "subject", as used herein, refers to all animals classified as mammals and includes, but is not restricted to, domestic and farm animals, primates and humans, e.g., human beings, non-human primates, cows, horses, pigs, sheep, goats, dogs, cats, or rodents. Preferably, the subject is a male or female human of any age or race.

The term "adrenoleukodystrophy, X-linked adenoleukodystrophy or X-ALD" as used herein refers to a rare, inherited leukodystrophy that leads to progressive damage to the brain, adrenal gland, peripheral nervous system, and eventually death. In a particular embodiment the adrenoleukodystrophy is selected from the group consisting of adult adrenomyeloneuropathy (AMN) with axonopathy in spinal cords, cerebral adrenomyeloneuropathy with brain demyelination (cAMN) and a childhood variant (cALD) characterized by severe cerebral demyelination. In a more preferred embodiment, the adrenoleukodystrophy is adrenomyeloneuropahy (AMN) (i.e. adult adrenomyeloneuropathy with axonopathy in spinal cords).

The term "adrenomyeloneuropathy (AMN)" as used herein refers to the adult adrenomyeloneuropathy with axonopathy in spinal cords variant of X-ALD. Said disease is characterized by several symptoms which include gradual, progressive weakness and stiffness of the legs, loss of the ability to coordinate muscle movement, weight loss, excessive muscle tone, difficulty in walking, visual defects, difficulty in articulating words, behavioural changes, adrenal insufficiency, seizures, sexual dysfunction/impotence, bladder dysfunction, mild peripheral neuropathy, and nausea.

The term "treatment", as used herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein). Thus, "treatment," "treating," and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or immune deficiency.

As the skilled person acknowledges, effectiveness of a specific mTOR inhibitor in X-ALD therapy is demonstrated by improved symptoms.

Alternative, the invention relates to the use of a specific mTOR inhibitor for the manufacture of a medicament for the prevention and/or treatment of X-ALD.

The term "specific mTOR inhibitor" has been previously described and the particulars thereof are incorporated herein by reference. In one embodiment, said specific mTOR inhibitor is a rapamycin-derivative. In a more particular embodiment, said specific mTOR inhibitor is temsirolimus.

The term "X-ALD" has been previously described and the particulars thereof are incorporated herein by reference. In a particular embodiment, said X-ALD selected from the group consisting of adult adrenomyeloneuropathy (AMN), cerebral adrenomyeloneuropathy (cAMN) and the childhood variant of adrenoleukodystrophy (cALD). In a more particular embodiment, the X-ALD is adult adrenomyeloneuropathy (AMN).

Compositions of the Invention

In another aspect, the invention relates to a composition comprising a specific mTOR inhibitor and a compound selected from the group consisting of an autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hypolipidemic drug.

The term "specific mTOR inhibitor" has been defined in the context of the first aspect of the invention and equally applies to the second aspect of the invention. In a particular embodiment, said specific mTOR inhibitor is a rapamycin-derivative. In a more particular embodiment, said rapamycin-derivative is temsirolimus. The terms "rapamycin-derivative" and "temsirolimus" have been previously defined.

The amount of the specific mTOR inhibitor, preferably temsirolimus, present in the composition of the invention may vary within a wide range, however, in a particular embodiment, the weight percentage of the specific mTOR inhibitor, preferably temsirolimus, with respect to the total composition of the invention is of at least 0.10% 0.50%, 1%, 2%, 3%, 4%, 5%, 6%, 7%, 8%, 9%, 10%, 15% 20%, 25%, 30%, 40%, 50%, 60%, 70%, 80%, 90%, or, at least, 95%.

The weight ratio of the inhibitor and the at least the second component of the composition in the composition of the invention may vary within a wide range, however, in general, the ratio is chosen, taking into account factors such as the condition being treated, the age, sex, weight, etc., of the subject who receives the inventive composition. Preferably, said weight ratio of the specific mTOR inhibitor of the invention, preferably temsirolimus, and the second component of the invention, that is a compound selected from the group consisting of an autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hipolipidemic drug, is one that results in a beneficial effect, in particular, an increase in the therapeutic effect of the composition of the invention relative to each of its components so that it can reach the same result with lower doses of each of the components, thereby reducing the side effects on the subject receiving the composition of the invention.

The term "mTOR-independent autophagy inducer" or "mTOR-independent autophagy enhancer" as used herein refers to any agent that can increase or stimulate autophagy in a cell by any pathway different from the mTOR pathway which induces autophagy. In some embodiments, an autophagy inducer can increase the formation of autophagosomes.

In a particular embodiment, said mTOR-independent autophagy inducer is selected from the group consisting of trehalose, ranitidine, spermidine, resveratrol, verapamil, loperamide, amidarone, trifluoperazine, monoxidil, 2'5'-dideoxyadenosine, tamoxifen, dimethylfumarate, thiazolinediones, 9-cis-retinoic acid, bexarotene, fluspirilene, trifluoperazine, penitrem A, pimozide, propranolol, vitamin E, α-lipoic acid, N-acetyl cysteine, lithium and combinations thereof.

The term "antioxidants", as used herein, refers to substances that reduce the levels of reactive oxygen species, for instance preventing the formation of such reactive oxygen species or removing them before they produce any damage. Examples of antioxidants include but are not limited to alpha-lipoic acid and N-acetylcisteine.

The term "antioxidants targeted to mitochondria", as used herein, refers to those antioxidants that are selectively concentrated within mitochondria in vivo. Examples of antioxidants targeted to mitochondria include but are not limited to mitoquinone (MitroQ) and [2-(3,4-dihydro-6-hydroxy-2,5,7,8-tetramethyl-2H-1-benzopyran-2-yl)ethyl]triphenylphosphonium bromide (MitoVitE).

The term "histone deacetylase inhibitors", as used herein, refers to substances that interfere with the function of histone deacetylase. Examples of histone deacetylase inhibitors include but are not limited to vorinostat, romidepsin, panobinostat, valproic acid, belinostat, mocetinostat, PCI-24781, entinostat, SB939, reminostat, givinostat, CUDC-101, AR-42, CHR-2845, CHR-3996, 4SC-202, CG200745, ACY-1215, sulforaphane and kevetrin.

The term "inhibitors of mitochondria transition pore opening", as used herein, refers to substances that block the non-specific increase in the permeability of the inner membrane of the mithocondria, caused by the opening of an inner membrane channel. Examples of inhibitors of mitochondria transition pore opening include but are not limited to cyclosporin A and derivatives thereof, NIM811, 2-aminoethoxydiphenyl borate and bongkrekic acid.

The term "anti-inflammatory drugs", as used herein, refers to substances that reduce inflammation. Examples of anti-inflammatory drugs include but are not limited to salicylates, such as acetylsalicylic acid, diflunisal and salsalate; propionic acid derivatives, such as ibuprofen, naproxen, fenoprofen, ketoprofen, dexketoprofen, flurbiprofen, oxaprozin, loxoprofen; acetic acid derivatives, such as indomethacin, sulindac, etodolac, ketorolac, diclofenac, nabumetone; enolic acid derivatives, such as piroxicam, meloxicam, tenoxicam, droxicam, lornoxicam and isoxicam; fenamic acid derivatives such as mefenamic acid, meclofenamic acid, flufenamic acid, and tolfenamic acid; selective COX-2 inhibitors such as celecoxib, rofecoxib, valdecoxib, parecoxib, lumiracoxib, etoricoxib and firocoxib; sulphonanilides such as nimesulide; and other compounds such as licofelone.

The term "PPAR agonists", as used herein, refers to substances that stimulate the peroxisome proliferator-activated receptors. Examples of PPAR agonists include but are not limited to GW-9662, thiazolidinediones, such as rosiglitazone; fibrates, such as bezafibrate, ciprofibrate, clofibrate, gemfibrozil and fenofibrate; and glitazars such as muraglitazar, tesaglitazar and aleglitazar.

The term "RXR agonists", as used herein, refers to substances that stimulate the retinoid X receptor. Examples of RXR agonists include but are not limited to CD 3254, docosahexaenoic acid, fluorobexarotene, bexarotene, retinoic acid and SR 11237.

The term "sirtuin 1 agonists", as used herein, refers to substances that stimulate the sirtuin 1 enzyme. Examples of sirtuin 1 agonists include but are not limited to resveratrol and SRT-1720.

The term "hypolipidemic agents", as used herein, refers to substances other than PPAR agonist and fibrates that lower the lipid low density lipoproteins (LDL) and/or increase the high density lipoprotein (HDL) in blood. Examples of hypolipidemic agents include but are not limited to statins, such as atorvastatin, cerivastatin, fluvastatin, lovastatin, mevastatin, pitavastatin, pravastatin, rosuvastatin, and simvastatin; niacin; bile acid sequestrants, such as cholestyramine, colesevelam and colestipol; other compounds such as phytosterols, ezetimibe, orlistat, and niacin.

In another aspect, the invention relates to the composition of the invention for use in medicine. Alternatively, the invention relates to the use of the composition of the invention for the manufacture of a medicament.

In a further aspect, the invention relates to the composition of the invention for use in the prevention and/or treatment of X-ALD in a subject.

Still alternative, the invention relates to a method for the prevention and/or treatment of X-ALD in a subject in need thereof that comprises the administration to said subject of a therapeutically effective amount of the composition of the invention.

The term "X-ALD" has been previously described and the particulars thereof are incorporated herein by reference. In a particular embodiment, the X-ALD is selected from the group consisting of adult adrenomyeloneuropathy (AMN), cerebral adrenomyeloneuropathy (cAMN) and the childhood variant of adrenoleukodystrophy (cALD). In a more particular embodiment, the X-ALD is adult adrenomyeloneuropathy (AMN).

Pharmaceutical Compositions

For their medical uses, the composition comprising a specific mTOR inhibitor defined in the second aspect of the invention may be found in a pharmaceutical composition.

Thus, in another aspect, the invention relates to a pharmaceutical composition comprising a therapeutically effective amount of the composition comprising a specific mTOR inhibitor and a compound selected from the group consisting of an mTOR-independent autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hipolipidemic drug, and a pharmaceutically acceptable excipient or carrier. The terms "mTOR-independent autophagy inducer", "antioxidant", "antioxidant targeted to mitochondria", "histone deacetylase inhibitor", "inhibitor of mitochondria transition pore opening", "anti-inflammatory drug", "PPAR agonist", "RXR agonist", "sirtuin 1 agonist" and "hipolipidemic drug", and the particulars thereof have been previously described and incorporated herein by reference.

The term "pharmaceutical composition", as used herein, refers to a composition comprising a therapeutically effective amount of the composition comprising a specific mTOR inhibitor according to the present invention and at least one pharmaceutically acceptable excipient or carrier.

The term "therapeutically effective amount" as used herein in relation to the agent of the invention, or in relation to the agent, excipient and/or carrier comprised by the pharmaceutical composition of the invention, relates to the sufficient amount of said agent, excipient and/or carrier to provide the desired effect, i.e. to achieve an appreciable prevention, cure, delay, reduction of severity or amelioration of one or more symptoms derived from a disease, and will generally be determined by, among other causes, the characteristics of the agent itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated.

The combination of compounds of the pharmaceutical compositions of the invention may be found as a prodrug, salt, solvate or clatrate, whether in an isolated dosage form or in combination with additional active agents.

The terms "pharmaceutically acceptable excipient", or "pharmaceutically acceptable carrier", refer to a non-toxic solid, semisolid or liquid filler, diluent, encapsulating material or formulation auxiliary of any conventional type. A pharmaceutically acceptable carrier is essentially non-toxic to recipients at the dosages and concentrations employed, and are compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants, which enhance the effectiveness of the formulation. Adjuvants could be selected from the group consisting of sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 22th Edition, 2012.

In a preferred embodiment of the present invention, the compounds of the pharmaceutical composition of the invention are formulated in accordance with standard procedures as a pharmaceutical composition adapted for delivered administration to human beings and other mammals. Typically, pharmaceutical compositions for intravenous or intraventricular administration are solutions in sterile isotonic aqueous buffer.

Where necessary, the pharmaceutical composition of the invention also includes a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampule of sterile water for injection or saline can be provided so that the ingredients may be mixed prior to administration.

In cases other than intravenous administration, the pharmaceutical composition can contain minor amounts of wetting or emulsifying agents, or pH buffering agents. The pharmaceutical composition can be a liquid solution, suspension, emulsion, gel, polymer, or sustained release formulation. The pharmaceutical composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules, nanoparticles, nanocapsules and the like.

In yet another preferred embodiment, therapeutics containing the pharmaceutical composition of the invention can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

Preferred excipients to be used in the present invention include sugars, starches, celluloses, gums and proteins. In a particular embodiment, the pharmaceutical composition of the invention will be formulated as a solid pharmaceutical dosage form (for example tablets, capsules, coated tablets, granules, suppositories, sterile crystalline or amorphous solids that can be reconstituted to provide liquid forms, etc.), liquid dosage form (for example solutions, suspensions, emulsions, elixirs, lotions, ointments, etc.) or semisolid dosage form (gels, pomades, creams and the like). Examples of pharmaceutically acceptable carriers are known in prior art and include phosphate buffered saline solutions, water, emulsions, such as oil/water emulsions, different types of humectants, sterile solutions, etc.

The pharmaceutical compositions containing the compounds according to the invention can occur at any pharmaceutical form of administration considered appropriate for the selected administration route, for example, by systemic, oral, parenteral or topical administration, for which it will include the pharmaceutically acceptable excipients necessary for formulation of the desired method of administration.

The effective quantity of the compounds of the invention can vary within a wide range and, in general, will vary depending on the particular circumstances of application, duration of the exposure and other considerations.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, the pharmaceutical compositions of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, pharmaceutical compositions of the invention may be administered in the form of transdermal patches or iontophoresis devices. In one embodiment, the compounds of the invention are administered as a transdermal patch, for example, in the form of sustained-release transdermal patch. Suitable transdermal patches are described in more detail in, for example, U.S. Pat. No. 5,262,165, U.S. Pat. No. 5,948,433, U.S. Pat. No. 6,010,715 and U.S. Pat. No. 6,071,531.

The pharmaceutical compositions of the invention can additionally include conventional excipients, i.e. pharmaceutically acceptable carriers suitable for parenteral application which do not react damaging with the active compounds. Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

Several drug delivery systems are known and can be used to administer the compounds or compositions of the invention, including, for example, encapsulation in liposomes, microbubbles, emulsions, microparticles, microcapsules, nanoparticles, nanocapsules and similars. The required dosage can be administered as a single unit or in a sustained release form.

Sustainable-release forms and appropriate materials and methods for their preparation are well known in the state of the art. In one embodiment of the invention, the orally administrable form of a pharmaceutical composition of the invention is in a sustained release form further comprises at least one coating or matrix. The coating or sustained release matrix include, without limitation, natural polymers, semi-synthetic or synthetic water-insoluble, modified, waxes, fats, fatty alcohols, fatty acids, natural semisynthetic or synthetic plasticizers, or a combination of two or more of the them.

Enteric coatings may be applied using conventional processes known to experts in the art.

Screening Methods of the Invention

In another aspect, the invention relates to a method for identifying a compound potentially useful for the treatment and/or prevention of X-ALD, hereinafter "the method of the invention", comprising:
 a) contacting an X-ALD cell with the candidate compound; and
 b) assaying a marker in the presence of said candidate compound, wherein the marker is selected from the group consisting of
  (i) mTOR activity levels and
  (ii) the expression level of an autophagosome marker,
wherein if said candidate compound inhibits the activity of mTOR and/or alters the expression of the autophagosome marker then the candidate compound is useful for the treatment and/or prevention of X-ALD.

The terms "mTOR", "treatment", "prevention" and "X-ALD" have been previously defined in the context of the first aspect of the invention and equally apply in the context of the screening methods of the invention.

According to the method of the invention, the first step comprises contacting an X-ALD cell with the candidate compound.

The expression "X-ALD cell", as used herein, refers to any single cell or alone or a as a plurality of cells (as a culture) or forming part of a 3D (three-dimensional) structure such an organotypic culture from an X-ALD patient wherein mTOR is overexpressed, giving rise an increased activation of the mTOR pathway.

The term "increased activation of mTOR pathway", as used herein, refers to cells wherein the activity and/or the expression of mTOR is increased in respect to a reference level, wherein said reference level is the expression and/or activity in cells which do not show an activation of mTOR pathway or which have not been stimulated with agents capable of activating the mTOR pathway. The term "mTOR pathway" also known as PI3K/AKT/mTOR pathway, as used herein, refers to a chain of proteins (PI3K, AKT and mTOR) in the cell that occurs when an extracellular signaling molecule activates a specific receptor located on the cell surface or inside the cell.

The X-ALD cell of the screening method of the invention has an mTOR expression level or activity level which is increased at least 10%, at least 20%, at least 30%, at least 40%, at least 50%, at least 100%, at least 200%, at least 300% or more with respect to a reference expression level or to a reference activity level. Methods for determining the expression level of mTOR or the mTOR activity have been previously defined in the context of the first aspect of the invention and are herein incorporated by reference.

In a particular embodiment, the cells of the screening method of the invention are transfected or genetically engineered to overexpress mTOR. In another particular embodiment, the cells of the screening method of the invention are obtained from X-ALD patients.

A cell is said to be "genetically modified", "transfected", or "genetically transformed" when a polynucleotide has been transferred into the cell by any suitable means of artificial manipulation, or where the cell is a progeny of the originally altered cell that has inherited the polynucleotide. The polynucleotide, i.e. a polynucleotide comprising the mTOR sequence, will often comprise a transcribable sequence encoding a protein of interest (i.e. mTOR), which enables the cell to express the protein at an elevated level. The genetic alteration is said to be "inheritable" if progeny of the altered cell have the same alteration. "Transformed cell" means a cell into which (or into predecessor or an ancestor of which) a nucleic acid molecule encoding a polypeptide of the invention has been introduced, by means of, for example, recombinant DNA techniques or viruses. "Nucleic acid" or "nucleic acid molecule" refer to a deoxyribonucleotide or ribonucleotide polymer in either single- or double-stranded form and, unless otherwise limited, can encompass known analogs of natural nucleotides that can function in a similar manner as naturally occurring nucleotides. The terms "polypeptide", "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but which functions in a manner similar to a naturally occurring amino acid.

Examples of cells that can be used in the method of the invention are, without limitation, primary cultures obtained from diverse tissues as brain, spinal cord, bone marrow, skin, blood, etc; immortalized cells obtained from primary cultures such as fibroblasts, B lymphocytes, T lymphocytes, monocytes and stem cells; modified cells obtained from primary cells such induced pluripotent stem cells, etc. In a preferred embodiment, the cells used are fibroblasts, more preferably human fibroblasts. In a still more preferred embodiment, the cells used in the method of the invention are human fibroblasts from X-ALD patients.

The cellular culture is maintained in conditions that permit the survival of the cells of said cultures. Said conditions include, between others, adequate humidity, temperature, gases concentration, nutrients (culture medium) etc. Special incubators, well known by the person skilled in the art, can be used for reaching the previously mentioned conditions. The culture conditions would be defined for each particular culture.

Illustratively, primary human fibroblast obtained from X-ALD patients are cultured in Dulbecco's Modified Eagle Medium supplemented with 10% fetal bovine serum, 100 U/ml penicillin and 100 µg streptomycin at 37° C. and 5% $CO_2$.

The expression "putting in contact or contacting an X-ALD cell with a candidate compound" refers to any process where the cell (or cells) is put in contact with the candidate compound to be assessed, and includes any possible in vitro way of putting extracellular in contact said compound or any way of introducing said compound to the cells. Thus, in the event that the candidate compound is a molecule with low molecular weight, it is enough to add said molecule to the culture medium. In the event that the candidate compound is a molecule with a high molecular weight (for example, biological polymers such as a nucleic acid or a protein), it is necessary to provide the means so that this molecule can access the cell interior. In the event that the candidate molecule is a nucleic acid, conventional transfection means can be used, as described previously for the introduction of the DNA construct. In the event that the candidate compound is a protein, the cell can be put in contact with the protein directly or with the nucleic acid encoding it coupled to elements allowing its transcription/translation once they are within the cell. To that end, any of the aforementioned methods can be used to allow its entrance into the cell. Alternatively, it is possible to put the cell in contact with a variant of the protein to be studied which has been modified with a peptide which can promote the translocation of the protein to the cell interior, such as the Tat peptide derived from the HIV-1 TAT protein, the third helix of the *Antennapedia homeodomain* protein from *D. melanogaster* or the VP22 protein of the herpes simplex virus and arginine oligomers.

The compound to be assayed is preferably not isolated but forms part of a more or less complex mixture derived from a natural source or forming part of a library of compounds. Examples of libraries of compounds which can be assayed according to the method of the present invention include, but are not limited to, libraries of peptides including both peptides and peptide analogs comprising D-amino acids or peptides comprising non-peptide bonds, libraries of nucleic acids including nucleic acids with phosphorothioate type non-phosphodiester bonds or peptide nucleic acids, libraries of antibodies, of carbohydrates, of compounds with a low molecular weight, preferably organic molecules, peptide mimetics and the like. In the event that a library of organic compounds with a low molecular weight is used, the library can have been preselected so that it contains compounds which can access the cell interior more easily. The compounds can thus be selected based on certain parameters such as size, lipophilicity, hydrophilicity, capacity to form hydrogen bonds.

The compounds to be assayed can alternatively form part of an extract obtained from a natural source. The natural source can be an animal, plant source obtained from any environment, including but not limited to extracts of land, air, marine organisms and the like.

The incubation of the test compound is made at different concentrations and times of incubation. The use of negative and positive controls is highly recommendable.

The second step of the screening method of the invention comprises assaying the activity of mTOR in the presence of said candidate compound; wherein the marker is selected form the group consisting of:
 (i) mTOR activity levels; and
 (ii) the expression level of an autophagosome marker.

Thus, in a particular embodiment, the second step of the method of the invention comprises assaying the activity of mTOR in the presence of said candidate compound by means of determining the mTOR activity levels. Thus, according to this embodiment of the method of the invention, the second step of the method for identifying a compound potentially useful for the treatment and/or prevention of X-ALD comprises determining the expression level of any substrates which are phosphorylated by mTOR such as EIF4EBP1, ULK1 or phosphorylated p70S6K proteins. The terms "EIF4EBP1", "ULK1" and "phosphorylated p70S6K" as well as suitable methods for determining said markers have been defined in the first context of the present invention and equally apply to this aspect of the invention.

According to the method of the invention, if said candidate compound inhibits the activity of mTOR, then the candidate compound is useful for the treatment and/or prevention of X-ALD.

In a particular and preferred embodiment of the invention, the activity of mTOR is determined by means of determining the level of P-p70S6K. In a preferred embodiment the level of phosphorylated p70S6K is determined by means of Western blot.

In general it is considered that the compound would be potentially useful for the treatment of X-ALD if the levels of P-p70S6K in the cell which is being assayed after the treatment of said cell with the candidate compound are lower than before the treatment.

In another particular embodiment, the second step of the method of the invention comprises determining the expression level of at least one autophagosome marker if the cell is a fibroblast. The term "autophagosome marker" or "autophagic marker" has been previously explained in the context of the first embodiment of the present invention.

The term "alters the expression" as used herein, means that the compound induces the expression of an autophagosome marker by more than 1 fold, more than 1.5 fold, more than 2 fold, or more than 2.5 fold relative to a negative control, such as cells which are not being treated with said compound. Said term also means that the compound reduces the expression of an autophagosome marker by more than 1 fold, more than 1.5 fold, more than 2 fold, or more than 2.5 fold relative to a negative control, such as cells which are not being treated with said compound.

As has been explained above, the specific mTOR inhibitor of the invention induces autophagy. In a particular embodiment, the method of the invention comprises the determination of the activity of mTOR by determining the expression level of an autophagosome marker selected form, LC3-II, p62 or combinations thereof. The terms "LC3-II" and "p62" as well as suitable methods for determining said markers have been defined in the first context of the present invention and equally apply to this aspect of the invention In general, it is considered that the compound would be potentially useful for the treatment of X-ALD if the compound alters the levels of LC3-II and p62 in respect with said levels measured in the cells which are not being treated with said compound. Thus, if the levels of p62 in the cell which is being assayed after the treatment of said cell with the candidate compound are lower than before the treatment, and/or if the levels of LC3-II in the cell which is being assayed after the treatment of said cell with the candidate compound are higher than before the treatment, then the compound can be considered useful for the treatment of X-ALD.

If desired, the screening method of the invention further comprises the determination of oxidative markers such oxidized proteins, chymotrypsin-like activity of the proteasome, expression levels of immunoproteasome subunits β1i/LMP2 and β5i/LMP7 and ATP levels. As has been explained above, a specific mTOR inhibitor prevents oxidized proteins accumulation and restores energetic levels in the cell. Thus, according to the method of the invention, the compound would be potentially useful for the treatment of X-ALD if, in addition to inhibit the activity of mTOR and/or to alter the expression of an autophagosome marker, the levels of oxidized proteins, the chymotrypsin-like activity of proteasome and/or the expression levels of the immunoproteasome subunits β1i/LMP2 and β5i/LMP7 in the cell which is being assayed after the treatment of said cell with the candidate compound are lower than before the treatment; and/or if the levels of ATP in the cell which is being assayed after the treatment of said cell with the candidate compound are higher than before the treatment. The terms "oxidative marker", "oxidized proteins", "chymotrypsin-like activity of proteasome", "immunoproteasome subunit β1i/LMP2", "immunoproteasome subunit β5i/LMP7", "ATP" and methods for their determination have been detailed in the context of the first method of the invention.

The inhibition of mTOR activity by means of a specific mTOR inhibitor prevents axonal degeneration. Thus, if desired, when the screening method of the invention is being assayed in a brain derived cell type, the second step of said method further comprises the determination of the expression level of at least one axonal damage marker selected from Iba-1, GFAP, synapthophysin, APP, 8-oxodG or combinations thereof. According to the present method, it is considered that the compound would be potentially useful for the treatment of X-ALD if it inhibits the activity of mTOR and if the levels of Iba-1, GFAP, synapthophysin, and/or APP in the cell that is being assayed after the treatment of said cell with the candidate compound, are lower than before the treatment. Regarding the determination of 8-oxdG levels, it is considered that the compound would be potentially useful for the treatment of X-ALD if it inhibits the activity of mTOR and if the levels of 8-oxodG in the cell which is being assayed after the treatment of said cell with the candidate compound are lower than before the treatment.

In a particular embodiment of the invention, the X-ALD is selected from the group consisting of adult adrenomyeloneuropathy (AMN), cerebral adrenomyeloneuropathy (cAMN) and the childhood variant of adrenoleukodystrophy (cALD). In a more particular embodiment, the X-ALD is adult adrenomyeloneuropathy (AMN).

The invention is detailed below by means of the following examples which are merely illustrative and by no means limiting for the scope of the invention.

EXAMPLES

Materials and Methods
  Antibodies and Reagents
  The following antibodies were used in Western blots: gamma-tubulin and DNP (2,4-dinitrophenylhydrazone) (Sigma); LC3 (Nanotools), anti-phospho-p70S6 kinase (Thr389), p70S6 kinase (Cell Signaling Technology); amyloid precursor protein (Boehringer); p62 and 8-oxodG (Abcam), GFAP, synaptophysin, goat anti-rabbit and anti-mouse IgG linked to horseradish peroxidase (DakoCytomation). The fluorogenic peptides: Suc-Leu-Leu-Val-Tyr-7-amido-4-methylcoumarin (Suc-LLVT-AMC) and 7-amino-4-methylcoumarin (AMC) were obtained from Calbiochem. Hexacosanoic acid (C26:0) and bafilomycin A1 were purchased from Sigma.

Human Brain Samples
  Brain tissues from patients with cerebral adrenomyeloneuropathy and healthy age matched male control subjects were obtained from the Brain and Tissue Bank for Developmental Disorders at the University of Maryland, Baltimore. Informed written consent was obtained from all patients or their legal representatives and the local ethics committee approved all the studies.

Mice and Behavioural Tests
  All methods employed in this study were in accordance with the Guide for the Care and Use of Laboratory Animals published by the US National Institutes of Health (NIH publication No. 85-23, revised 1996) and the ethical committees of IDIBELL and the Generalitat de Catalunya. The generation and genotyping of Abcd1 null mice have been previously described. Mice used for experiments were on a pure C57BL/6J background. Abcd1 null and wild type mice were separated into control and treated groups. Temsirolimus (LC laboratories) was administered by intraperitoneal injections three times a week at a dose of 20 mg/kg for 3 months with alternate 3-weeks rest periods between each month of treatment. Control mice were given a placebo injection containing buffer only with the same frequency. Treadmill test was carried out exactly as previously described (López-Erauskin J, et al, 2011, Ann Neurol 70, 84-92). The latency to falling off the belt (time of shocks in seconds) and the number of received shocks were measured. Bar cross test was performed as previously described (López-Erauskin J, et al, 2011, Ann Neurol 70, 84-92). Placebo and drug treated mice within each litter were tested on the treadmill simultaneously and at the time of testing were not identified as to their treatment status.

Cell Culture and Treatment
  Skin biopsies to prepare fibroblasts were collected according to the institutional guidelines for sampling, including informed consent from the persons involved or their representatives. Primary human fibroblasts were cultured in DMEM (containing 10% fetal bovine serum, 100 U/ml penicillin and 100 μg streptomycin) at 37° C. in humidified 5% CO2/95% air. Unless otherwise stated, experiments were carried out with cells at 80% confluence. For starvation conditions (high proteolysis medium, H), cells were switched, after washing, from full growth medium (see above, low proteolysis medium, L) to Krebs-Henseleit medium (118.4 mM NaCl, 4.75 mM KCl, 1.19 mM KH$_2$PO4, 2.54 mM MgSO$_4$, 2.44 mM CaCl$_2$.2H2O, 28.6 mM NaHCO$_3$, 10 mM glucose) containing 10 mM Hepes, pH 7.4 (high proteolysis medium, H) and incubated for 4 h or less at 37° C.

Autophagy Analysis in Cultured Cells

For pulse-chase experiments, human control and X-ALD patient fibroblasts were incubated for 48 h in fresh full medium with 1 µCi/ml [3H]valine (Hartmann Analytic Gmbh), followed by a 24 h chase in fresh full medium containing 10 mM L-valine to degrade short-lived proteins. Then, all cultures were incubated for the indicated times in Krebs-Henseleit medium with 10 mM Hepes, pH 7.4, containing 10 mM valine and the indicated additions. Protein degradation, which was analysed 1 h later to ensure maximal effects of the various additions and for only 3 h to avoid possible secondary effects, was calculated at two intervals of 1.5 h by measuring the net release of trichloroacetic acid-soluble radioactivity from the labelled cells into the culture medium and expressed as percentage of protein degraded. The contribution of lysosomal degradation to total protein degradation was calculated using 20 mM NH4Cl (Sigma-Aldrich) plus 100 µM leupeptin (Peptide Institute), as previously described (Fuertes G, et al, 2003, Biochem J 375, 75-86).

Autophagic flux was assessed by measuring, with specific antibodies, endogenous LC3-II levels relative to γ-tubulin levels after 4 h in the presence of 400 nM bafilomycin A1. Autophagy was also assessed transfecting human fibroblasts with pEGFP-LC3 cells and, after 48 h, the number of fluorescent dots per transfected cells were counted with a fluorescence microscope as previously described.

Reverse Transcription (RT)-PCR Analysis

Total RNA was isolated from homogenized spinal cord using the RNeasy mini kit (Qiagen), according to the manufacturer's instructions. RNA samples with RNA Integrity Number (RIN) above 8 and 28S/18S ratio higher than 1 were used for the experiments. Then, first strand cDNA was synthesized for each RNA sample using Superscript II reverse transcriptase (Invitrogen) and random primers. The expression of the candidate proteasome genes was analysed by RQ-PCR using TaqMan® Gene Expression Assays (Applied Biosystems).

Relative quantitation was carried out using the 'Delta-Delta Ct' (ΔΔCt) method with tubby RNA as endogenous control. Transcript quantification was performed in duplicate for each sample.

Immunohistochemistry

Spinal cords were harvested from 20-month-old mice (wild type, Abcd1−/−/Abcd2−/− and Abcd1−/−/Abcd2−/− treated with temsirolimus), after perfusion with 4% paraformaldehyde and prepared and incubated for immunohistochemistry as described (López-Erauskin J, et al, 2011. Ann Neurol 70, 84-92).

Electron Microscopy

L1-L2 sections of mouse spinal cord were fixed in 3% glutaraldehyde/4% PFA in phosphate buffer (100 mM phosphate buffer, pH 7.4) at 4° C. for 24 h. Vibratome sections (50-100 µm thick) were post-fixed in 1% osmium tetroxide, suspended in 2% (w/v) aqueous uranyl acetate for 1 h, washed three times in distilled water, dehydrated through a graded acetone series of 30, 50 70, 90 and 100% and embedded in Durcupan ACM (Electron Microscopy Sciences) by standard procedures. To select the area of interest, semithin sections (1.5 µm) were first obtained with a diamond knife and stained with 1% toluidine blue. Ultrathin sections were then cut and stained with lead citrate and observed in a Philips CM-10 electron microscope at 60 kV. Counts of lysosomes were made per genotype on more than thirty electron micrographs (final magnification: ×7,000) taken at random from four different mice.

Electrophoresis and Western Blotting

Tissues were removed from euthanized mice and flash-frozen on liquid nitrogen. Frozen tissues and human fibroblasts samples were homogenized in RIPA buffer (Cell Signaling Technology) using a motor-driven grinder (Sigma-Aldrich), and then sonicated for 2 min at 4° C. in an Ultrasonic processor UP50H (Hielscher-Ultrasound Technology). Samples were subjected to polyacrylamide (10% acrylamide) gel electrophoresis for 60 min at 120 mV. Resolved proteins were transferred onto nitrocellulose membranes and proteins were detected with ECL Western blotting analysis system followed by exposure to CL-XPosure Film (Thermo Scientific). Autoradiographs were scanned and quantified using a GS800 Densitometer (Bio-Rad).

Other Procedures

ATP levels were measured as previously described (Galino J, et al 2011, Antioxid Redox Signal 15, 2095-2107). For proteasome activity assays, tissues were homogenized in an ice-cold buffer (50 mM Tris-HCl pH 7.5, 1 mM dithiothreitol, 0.25 M sucrose, 5 mM MgCl$_2$, 0.5 mM EDTA with 2 mM ATP), using a teflon-on-glass homogenizer, and centrifuged at 12,000×g for 10 min. Chymotrypsin-like activity of proteasomes was determined as described (Launay N, et el, 2013 Brain 136, 891-904), using Suc-LLVY-AMC as substrate. Equal amounts of extracts were incubated with the substrate (100 µM) in 100 µl of proteasome activity assay buffer (0.5 mM Tris-HCl, pH 7.8, 10 mM MgCl2, 1 mM dithiothreitol with or without 5 mM ATP) for 30 min at 37° C. The reactions were quenched by adding 0.9 ml of cold ethanol. The free AMC fluorescence was quantified with a fluorescence multiplate FLUOstar OPTIMA FL reader (BMG) with excitation and emission wavelengths at 380 and 460 nm, respectively. Lactacystin (5 µM, 2 h) was employed to ensure the specificity of the assays. All reactions were carried out in duplicate and readings were calibrated using standard solutions of the fluorophores.

Statistical Analysis

Statistical significance was assessed using the Student's t-test whenever two groups were compared. When analyzing multiple groups, we used ANOVA and Tukey's post hoc test to determine statistical significance. Data are presented as mean±SD. A p<0.05 was considered significant (*p<0.05; p<0.01; *p<0.001).

Example 1: Autophagy is Impaired in X-ALD Patients and in X-ALD Mouse Models

The expression patterns of two molecular indicators of autophagy in patients who suffered the cerebral forms of X-ALD, cCALD and AMN were examined. During activation of macroautophagy, the cytosolic protein LC3-I is converted by lipidation into LC3-1 and associates specifically to both sides of the limiting membranes that form the autophagosome. LC3-II does not bind other organelles and is degraded in an autophagy-dependent fashion in lysosomes. When the levels of LC3-II in non-affected and affected brain areas from cCALD and cAMN patients and in control samples were assessed (FIGS. 1A and B), they were consistently lower in both non-affected and affected brain areas of patients. Since without lysosomal inhibitors LC3-II levels depend on the rates of both formation of autophagosomes and conversion into autolysosomes, this decrease may indicate either an autophagy impairment or an increased autophagosome-endosome/lysosome fusion. Therefore, levels of the multifunctional protein p62 (also called SQSTM1), a protein involved in aggresome formation that can be degraded by autophagy was also measured. The expression level of p62 is elevated in non-affected areas and more prominently in affected zones from both cCALD and cAMN patients (FIGS. 1A and B). All these results support that autophagy is impaired in X-ALD patients.

Both autophagy markers were analyzed in the X-ALD mouse model at the different stages of the disease. The mouse model for X-ALD is a classical knockout of the ABCD1 gene (Abcd1 null), which exhibits a late-onset axonopathy in the spinal cord without overt inflammatory features or demyelination, thus resembling adult onset adrenomyeloneuropathy in humans. Abcd1 null mice present overt motor disabilities and a neuropathological phenotype at 20-22 months of age, although oxidative damage appears very early, at around three months of age. Impaired autophagy in spinal cord of 12-month-old Abcd1 null mice was found, as evidenced by decreased LC3-II levels and elevation of p62 levels compared to the wild type mice (FIG. 1C). These differences were not found to be significant in 3-month-old Abcd1 null mice when compared to wild type (FIG. 1C).

Figure 2:
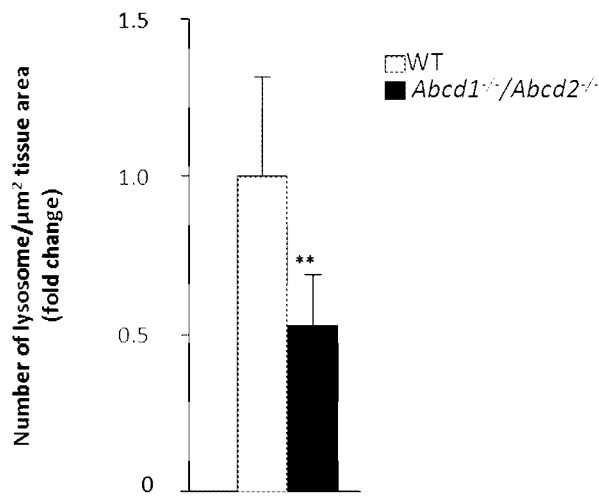
FIG. 2: Measurement of the number of lysosomes in samples from spinal cord of 20 month old WT and Abcd1−/− Abcd2−/− mice. The number of lysosomes per μm$^2$ tissue is shown as mean±SD from three independent mice per genotype and is expressed relative to the WT values. **p<0.01.

Double knock-out (Abcd1−/−/Abcd2−/−) mice present an overt neuropathological phenotype at 16 months of age and are used as a bona fide surrogate for the Abcd1 null mouse (López-Erauskin J, et al., 2011, Ann Neurol 70, 84-92). There was a clear diminution (by about 50%) of lysosomes in Abcd1−/−/Abcd2−/− mouse spinal cord (FIG. 2), a result that is compatible with the observed decrease in autophagy.

Example 2: Autophagy is Impaired in Fibroblasts from X-ALD Patients

Figure 3:
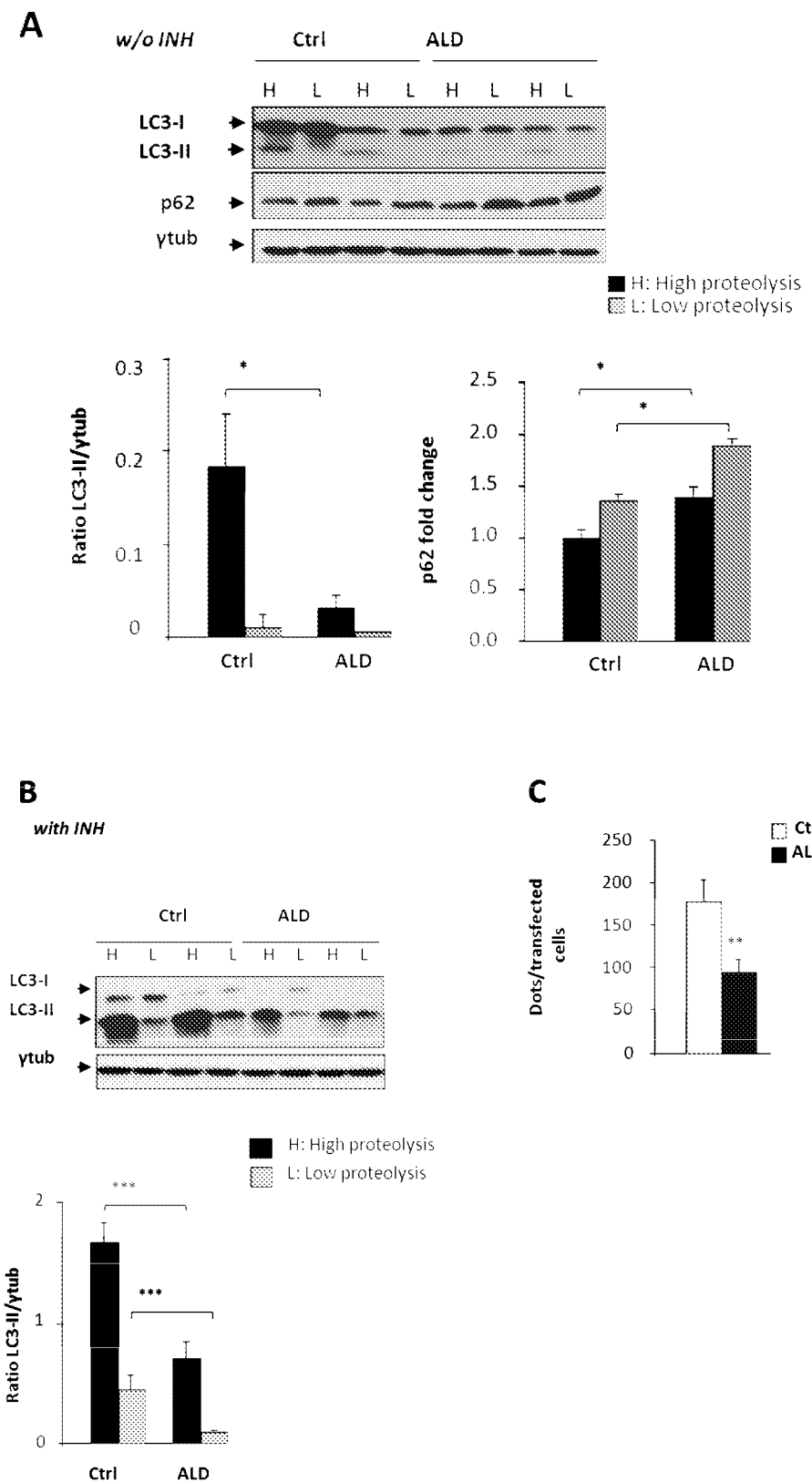
FIG. 3: (A) Representative Western blots of LC3 and p62 in extracts from control (Ctrl) and patients (ALD) fibroblasts incubated under high (H) and low (L) proteolysis conditions. (B) LC3 levels were also investigated under the same conditions, but in the presence of the lysosomal inhibitor bafilomycin A1. In the LC3 Western blots, the position of the LC3-I and LC3-II bands are indicated on the left and γ-tubulin (γtub) was used as a loading control. The histograms show the quantification of LC3-II bands referred to the γtub levels (in A and B) and the p62 levels relative to Ctrl under high proteolysis conditions (in A). All data represent the mean±SD of 4 independent experiments. (C) Quantification from representative fluorescence images of control (Ctrl) and patients' (ALD) fibroblasts transfected with EGFP-LC3 and incubated, 48 h after transfection, in high proteolysis medium for 2 h at 37° C. The histogram represents the number of fluorescent dots per transfected cell as the mean±SD of 3 independent experiments (at least 50 transfected cells were counted per experiment). The number of fluorescent dots is lower in the ALD fibroblasts. *$p<0.05$, $p<0.01$ and *$p<0.001$.

To assess autophagy in X-ALD fibroblasts, cells were cultured, as previously described (Fuertes G, et al, 2003, Biochem J 375, 75-86), either in serum- and amino acid-free medium (Krebs-Henseleit medium) to stimulate autophagy via the well described starvation response (H: high proteolysis) or in full medium to asses basal autophagy (L: low proteolysis). The results demonstrated that fibroblasts from X-ALD patients had compared to controls increased p62 levels and lower levels of LC3-II, the latter especially in high proteolysis (H) medium (FIG. 3A). As the observed variations in the levels of LC3-II, in FIG. 3A and also in FIG. 1, can be due to a change in synthesis or in degradation of the protein, human fibroblasts were treated with the lysosomal inhibitor bafilomycin A1 to block LC3-II degradation. Under these conditions, the levels of LC3-11 correlate with the number of autophagosomes in the cells. In the presence of bafilomycin A1, fibroblasts from X-ALD patients had again lower levels of LC3-II compared to control fibroblasts, in both full (L) and starvation (H) media (FIG. 3B). The decrease in autophagosomes was confirmed by a reduction (by about 50% compared to control fibroblasts) in the number of fluorescent puncta in X-ALD fibroblasts that transiently expressed EGFP-LC3 (FIG. 3C).

Therefore, overall these results support an impairment in autophagic flux in the fibroblasts from X-ALD patients.

Example 3: mTOR Activity is Enhanced in Abcd1$^{-/-}$ Mice

Figure 4:
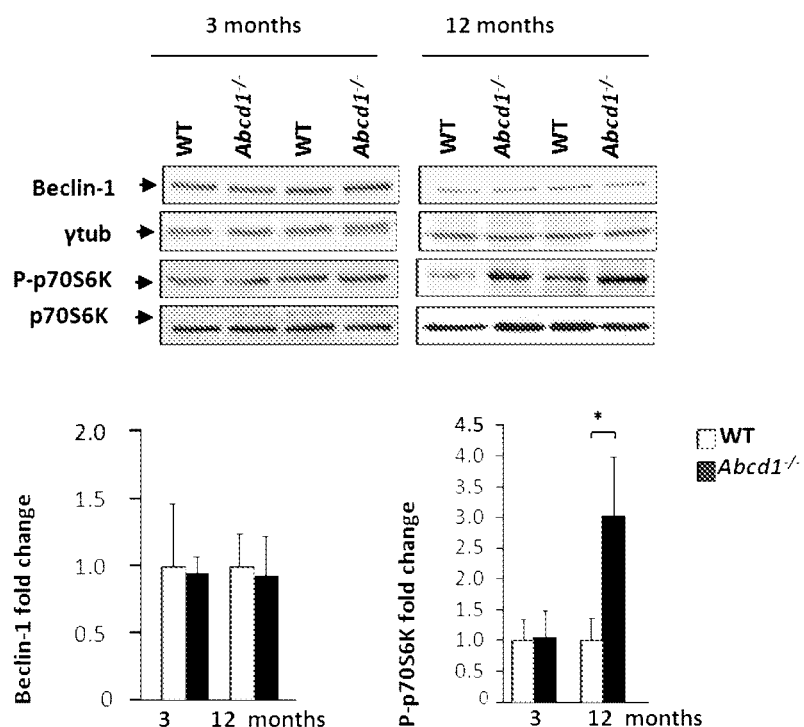
FIG. 4: (A). Representative Western blots of BECLIN-1 and of total p70S6K and its phosphorylated form (P-p70S6K) in spinal cord of 3 and 12 month-old WT and Abcd1−/− mice. γ-tubulin (γtub) was used as a loading control. (B) The phosphorylation of p70S6K was also investigated in fibroblasts from control individuals (Ctrl) and patients (ALD). Cells were incubated in high (H) and low (L) proteolysis media. The histograms show BECLIN-1 levels (in A) and P-p70s6K/p70S6K ratios (in A and B). Data are expressed relative to 3 months-old WT mice (in A) and Ctrl fibroblasts (in B) and represent the mean±SD of 6 (A) or 4 (B) independent experiments. *$p<0.05$ and ***$p<0.001$.
Figure 4:
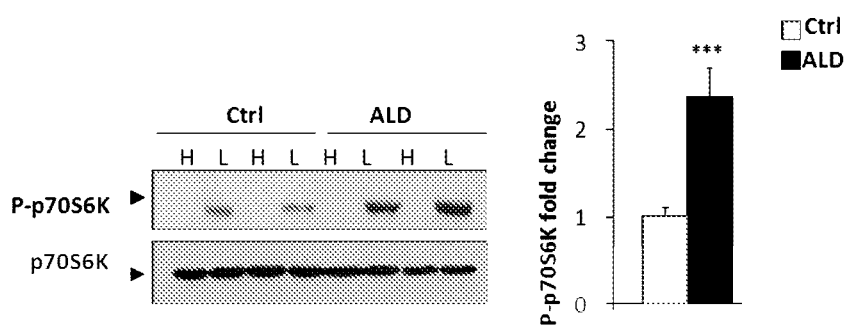

The mechanism of autophagy impairment during X-ALD progression was investigated. Class III PI3 kinase complex includes BECLIN-1 and controls the generation of preautophagosomal structures. Since it has been shown that a lower expression of BECLIN-1 is associated with a reduced autophagic vacuole formation, BECLIN-1 levels in the X-ALD mouse model were first analyzed. No significant differences were observed at 3 or 12 months in Abcd1−/− mouse spinal cord compared to wild type mice (FIG. 4A). The activation state of mTOR, a major negative regulator of macroautophagy was also investigated. This kinase inhibits autophagy under nutrient-rich conditions. Analysis of p70S6K, a well-established mTOR substrate, showed increased phosphorylation of the protein in spinal cord of 12-month-old, but not of 3-month-old, Abcd1−/− mice, compared to control mice (FIG. 4A), in good agreement with the results shown in FIG. 1C. Similarly, analysis of p70S6K phosphorylation in X-ALD fibroblasts showed, under basal conditions (low proteolysis medium, L), a significant increase in comparison to control fibroblasts (FIG. 4B). As expected, no activity of mTOR was detected in the fibroblasts under starvation conditions (high proteolysis medium, H).

Therefore, since mTOR inhibits autophagy, these results strongly suggest that the autophagy defect observed in X-ALD is mTOR-dependent.

Example 4: VLCFA Impairs Autophagy in Human Fibroblasts

Figure 5:
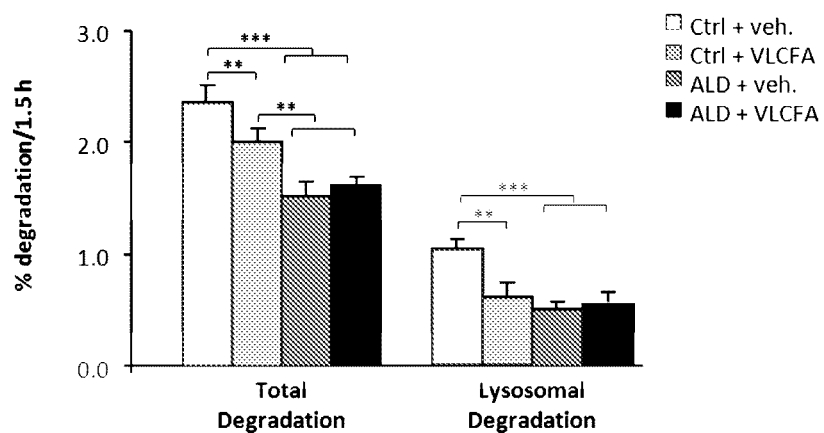
FIG. 5: (A) Control (Ctrl) and patient's (ALD) fibroblasts, vehicle (veh.)-treated (negative control) or treated with VLCFA (C26:0, 50 μM 24 h), were labelled with [³H]valine in high proteolysis medium and total and lysosomal degradation of long-lived proteins were measured. Results are presented as the percentage of the labelled protein that is degraded per 1.5 h and represent the mean±SD of 4 independent experiments. (B) Representative Western blots of LC3 and p62 in Ctrl and ALD fibroblasts treated (+) or not (−, veh. treated) with VLCFA. The position of the LC3-I and LC3-II bands are indicated on the left of the LC3 Western blot and γ-tubulin (γtub) was used as a loading control. The histograms show the quantification of LC3-II referred to the γtub levels and the p62 levels relative to those in Ctrl fibroblasts. Data represent the mean±SD of 4 independent experiments. $p<0.01$ and *$p<0.001$.
Figure 5:
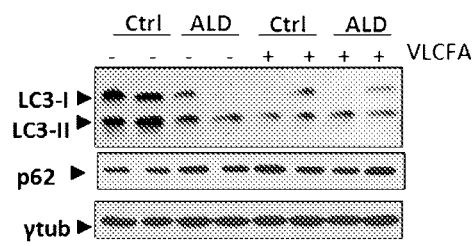
Figure 5:
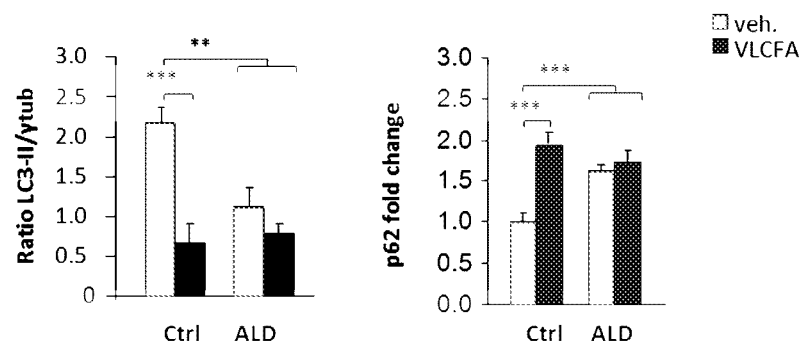

In X-ALD, VLCFA accumulate. The effect of the addition of an excess of hexacosanoic acid to fibroblasts isolated from controls and X-ALD patients was tested. First, the degradation of intracellular proteins was analyzed to determine if it was any alteration in control and X-ALD fibroblasts upon addition of an excess of VLCFA, by analyzing in pulse-chase experiments the degradation of long-lived proteins under starvation. Total protein degradation and also, separately, lysosomal protein degradation were estimated by procedures previously described (Fuertes G, et al, 2003, Biochem J 375, 75-86). As shown in FIG. 5A, total degradation of long-lived proteins is diminished (about 35%) in X-ALD fibroblasts compared to control fibroblasts.

Similarly, lysosomal degradation, which under these high proteolysis conditions mainly corresponds to macroautophagy (Fuertes G, et al., 2003 Biochem J 375, 75-86), was markedly decreased (about 50%) to reach the basal level in X-ALD fibroblasts. These results confirm with other procedures the impairment in autophagy in X-ALD detected above. Upon addition of an excess of VLCFA, total and lysosomal degradation were inhibited, about 15 and 40%, respectively, in control fibroblasts, while no significant inhibitions were observed in X-ALD fibroblasts (FIG. 5A).

Then, the LC3-II and p62 levels in cell extracts from control and X-ALD fibroblasts treated or not with VLCFA were determined by immunoblot analysis. In control fibroblasts, an excess of VLCFA induced a marked decrease of LC3-II levels and an increase in those of p62 levels, whereas no significant differences were found upon addition of a VLCFA excess to X-ALD fibroblasts in the already altered LC3-II and p62 levels (FIG. 5B).

These results are in agreement with the pulse-chase experiments and, thus, suggest that the increase in VLCFA that occurs in X-ALD contributes to the observed impairment of autophagy in the disease.

Example 5: An Antioxidant Treatment Partially Restores Autophagy in Abcd1$^{-/-}$ Mice Starting at about 15 months of age, Abcd1 null mice present motor disabilities and neuropathological signs, although oxidative damage appears very early in life, at around three months of age (Fourcade S et al., 2008. Hum Mol Genet 17, 1762-1773). A combination of vitamin E, α-lipoic acid and N-acetyl cysteine (NAC) efficiently reduced reactive oxygen species (ROS) production in vitro, reversed oxidative damage to proteins and DNA in spinal cords and arrested axonal degeneration and motor disability in X-ALD mice (López-Erauskin J, et al, 2011, Ann Neurol 70, 84-92).

Figure 6:
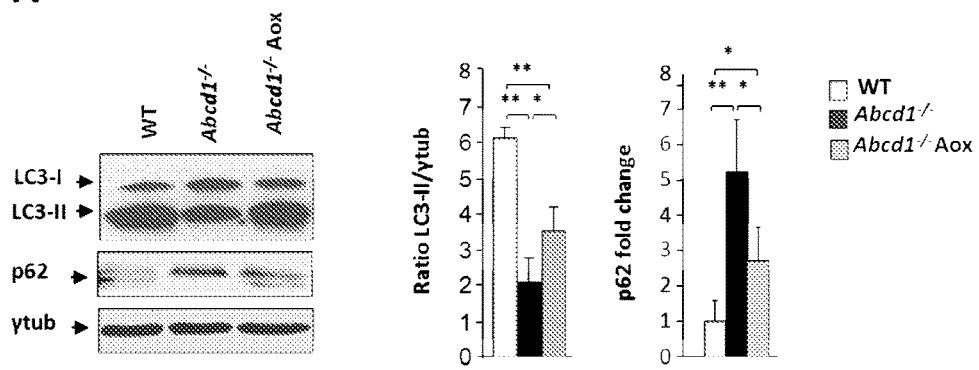
FIG. 6: (A) WT and Abcd1−/− mice treated or not for 4 months with an antioxidant mixture (Aox, vitamin E, α-lipoic acid and N-acetyl cysteine) increases LC3-II levels and partially prevents the accumulation of p62 in Abcd1−/− mouse spinal cord, as shown by Western blotting with specific antibodies. The position of the LC3-I and LC3-II bands are indicated on the left of the LC3 Western blot and, as a loading control, γ-tubulin (γtub) was used. (B) The effect of the antioxidant treatment from A (Aox) on the activity of mTOR was also investigated in spinal cord of Abcd1−/− mice at 12 months. Representative Western blot of the levels of total p70S6K and its phosphorylated form (P-p70S6K) using specific antibodies in WT and Abcd1−/− mice treated or not with antioxidants. In A and B, the histograms show the quantification of LC3-II referred to γtub and the p62 levels relative to WT (A) and the P-p70s6K/p70S6K ratios (B). Data represent the mean±SD of 6 independent experiments. *$p<0.05$ and **$p<0.01$.
Figure 6:
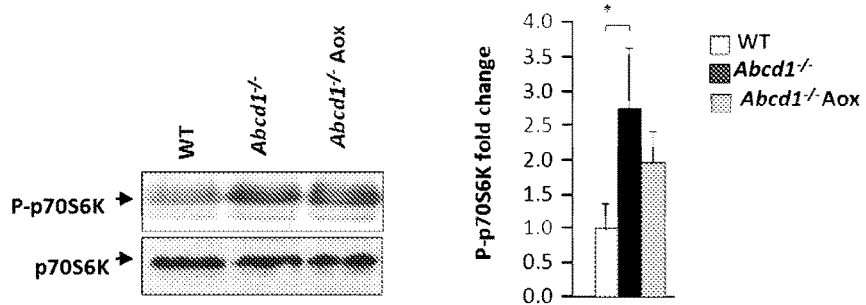

Treatment of mice with this antioxidant cocktail over four months produced significant increases and decreases, respectively, of LC3-II and p62 levels in Abcd1−/− mouse spinal cord (FIG. 6A). This indicates that antioxidants prevent, at least in part, the downregulation of macroautophagy in Abcd1−/− mice. The effect of the antioxidant treatment on the activity of mTOR was also investigated. As shown in FIG. 6B, although the increased phosphorylation of p70S6K observed in 12 month-old Abcd1−/− mice (see also FIG. 4A) were slightly reduced by the antioxidant treatment, the effect was not significant. This underscores that autophagy may be induced by mechanisms independent of mTOR in X-ALD, and suggests that autophagy activators in general (including mTOR inhibitors) may be valuable tools to treat adrenoleukodystrophy.

Example 6: Temsirolimus Promotes Autophagy in Abcd1$^{-/-}$ Mice

As the mTOR inhibitor rapamycin is a well-known autophagy inducer, we tested in vivo its potential therapeutic effect on X-ALD pathogenesis. Because rapamycin has poor water solubility and stability in aqueous solution, the rapamycin ester temsirolimus was used.

10 month-old Abcd1 null mice were treated with temsirolimus, or vehicle (control), administered by intraperitoneal injection as described previously. Doses tests in order to check mice's body response was firstly performed. Continuous administration of temsirolimus during 3 months leaded to important weight losses (data not shown). Thus, to prevent side effects other treatment conditions: intraperitoneal injections of temsirolimus for 3 months with alternate 3-weeks rest periods between each month of treatment, were tested. Under these conditions, better locomotor performances without significant weight loss were observed in mice, indicating that this treatment was more suitable.

Figure 7:
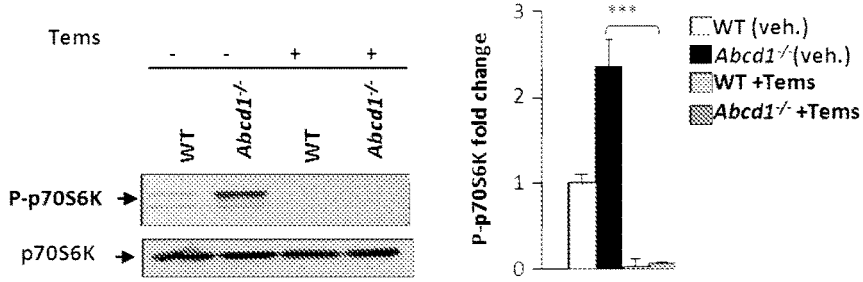
FIG. 7: (A)-(C): Representative Western blots analyzing with specific antibodies p70S6K phosphorylation (A) and the levels of LC3-II and p62 (B) and oxidized proteins (C), detected with anti-DNP antibodies, in spinal cord of 14 month-old WT and Abcd1−/− mice treated (+) or not (−, vehicle, veh.) with temsirolimus (Tems). As loading controls, total p70S6K (A) and γ-tubulin (γtub) (B and C) were used and the position of the LC3-I and LC3-II bands are indicated on the left of the LC3 Western blot in (B). The histograms show the P-p70s6K/p70S6K ratios relative to WT (A), the quantification of LC3-II referred to the γtub levels and the p62 levels relative to WT (B) and the ratio of oxidized proteins (Ox-proteins) relative to WT (C). All data represent the mean±SD of 6 independent experiments. (D): Measurements of ATP levels in WT and Abcd1−/− spinal cord from mice treated as above. Data are expressed relative to WT and represent the mean±SD of 6 independent experiments. (E) and (F): Chymotrypsin-like (CTL) proteasome activities measured with or without ATP (+ATP and −ATP, respectively) (E), and RT-PCR with specific primers for the indicated 20S and i-20S subunits (F) were determined in lysates from spinal cord of wild-type (WT) and Abcd1−/− mice untreated (veh.) or treated with temsirolimus (Tems) as above. Data are expressed relative to WT and represent the mean±SD of 4 different mice per genotype. In A-F, *$p<0.05$, $p<0.01$ and *$p<0.01$.
Figure 7:
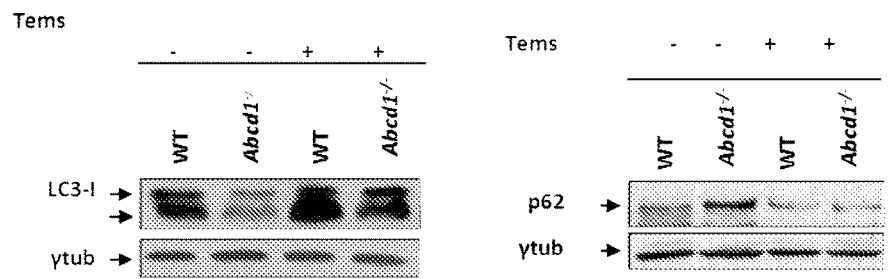
Figure 7:
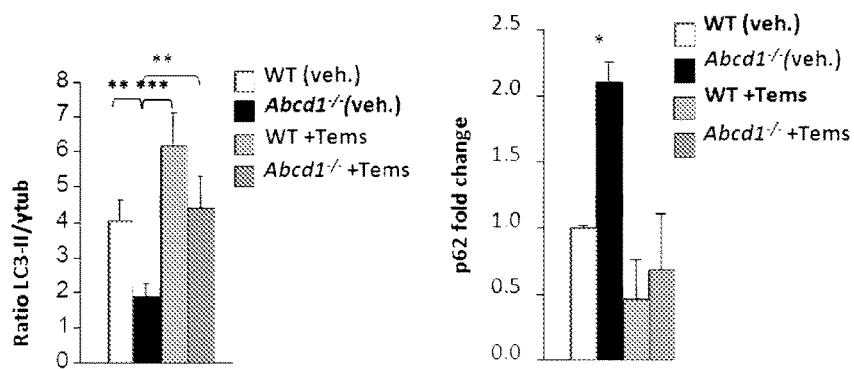
Figure 7:
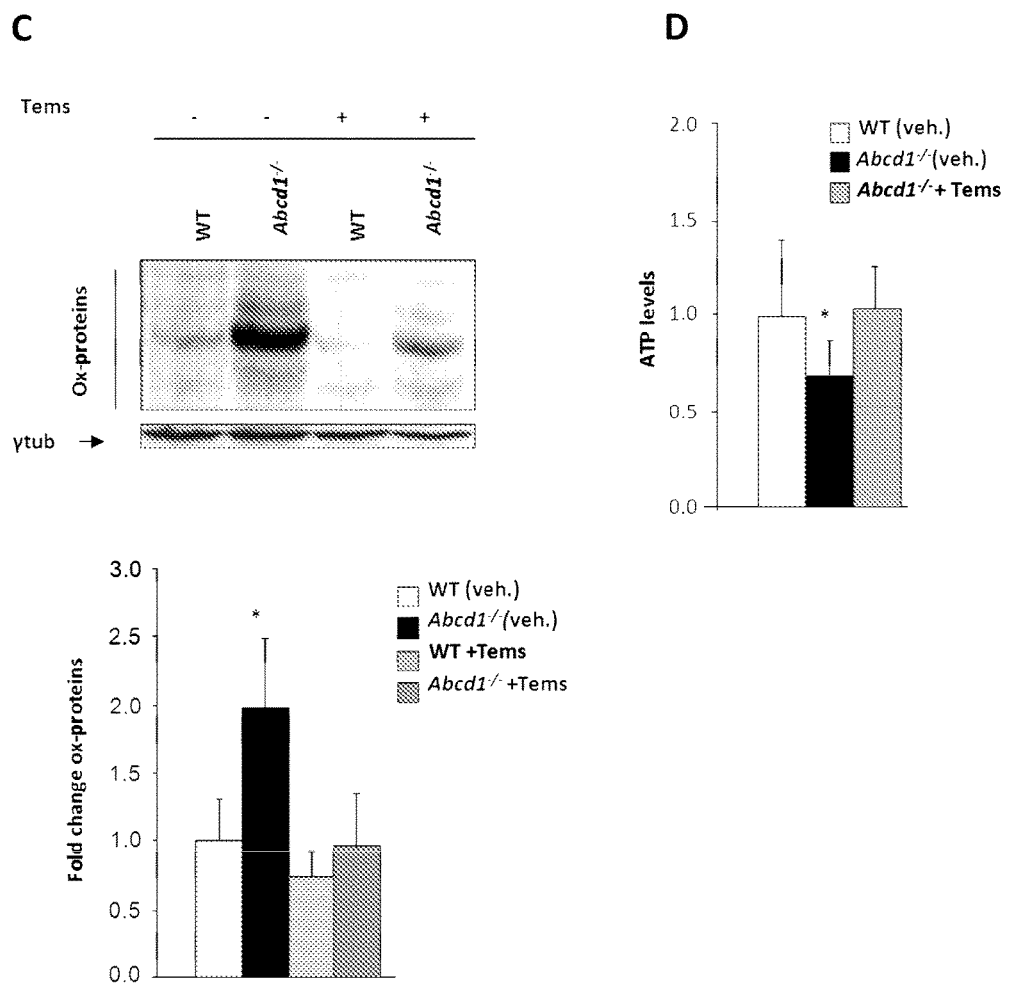
Figure 7:
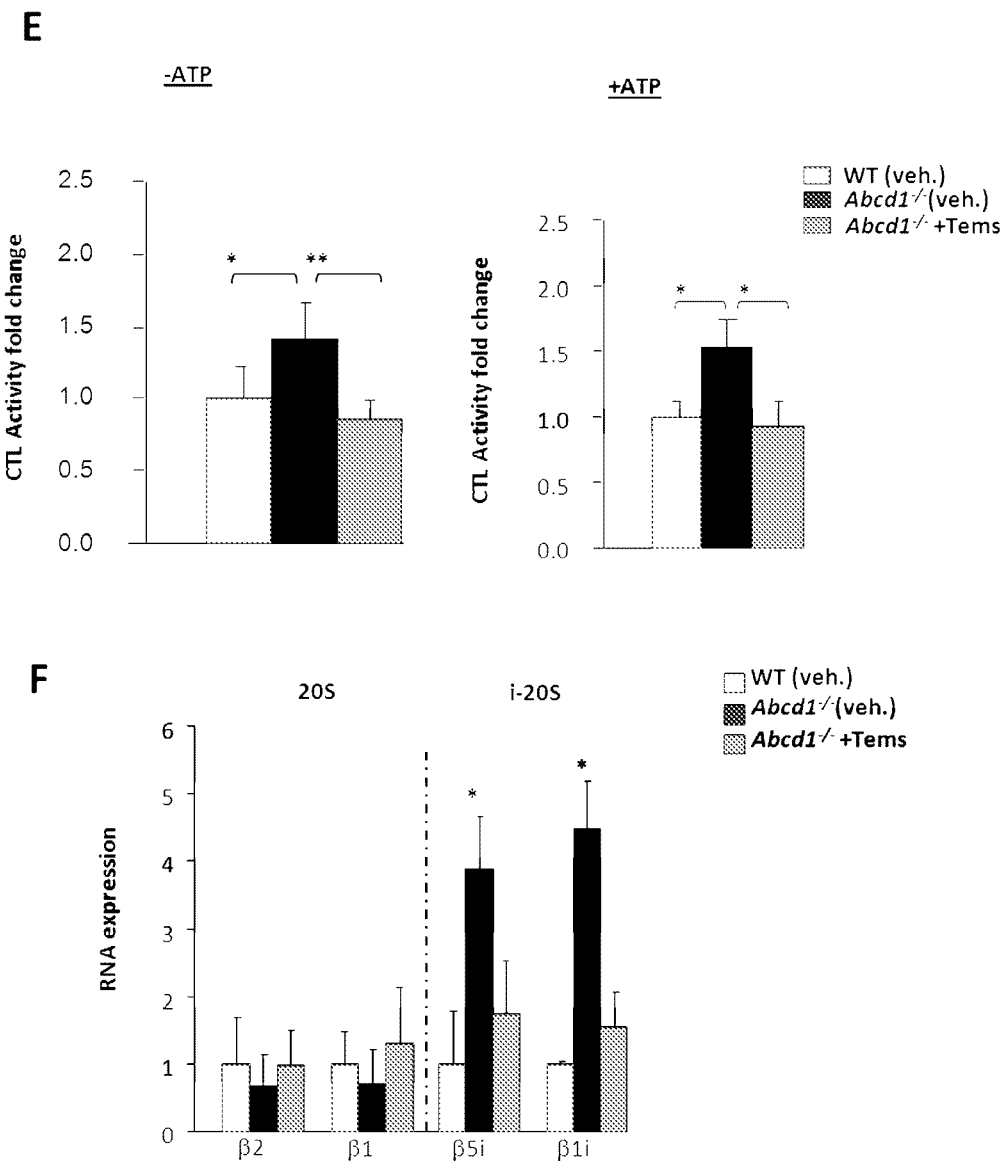

To assess the effect of temsirolimus in X-ALD, first the inhibition of the mTOR pathway in the spinal cord of treated mice was confirmed. As expected, mice treated with temsirolimus showed a decrease of phosphorylated p70S6K, while immunoreactivity for total p70S6K did not change (FIG. 7A).

Autophagy was also assessed measuring in Western blots LC3-II and p62 levels, which were shown to be, respectively, up- and down regulated by temsirolimus in Abcd1−/− mice spinal cord (FIG. 7B) as expected from the inhibition of mTOR.

Example 7: Temsirolimus Prevents Oxidized Proteins Accumulation, Energetic Failure and Proteasomal Alterations in Abcd1$^{-/-}$ Mice Oxidative stress contributes to the progression of X-ALD. There are signs of oxidative damage in spinal cords from the X-ALD mouse model and in fibroblasts from X-ALD patients, with direct oxidative, glycoxidative and lipoxidative damage to proteins and altered enzymatic antioxidant defenses (Fourcade S, et al, 2008. Hum Mol Genet 17, 1762-1773).

In addition, oxidative damage specifically affects ATP levels which are significantly diminished in Abcd1 null mice and in fibroblasts from X-ALD patients, implying that oxidative stress provoked by VLCFA results in impairment of energy metabolism (Galino J, et al, 2011, Antioxid Redox Signal 15, 2095-2107). Here, it is demonstrated that temsirolimus treatment reduced considerably the levels of oxidized proteins in Abcd1−/− mouse spinal cord (FIG. 7C) and prevented the bioenergetic failure, normalizing the ATP levels (FIG. 7D).

Finally, malfunctioning of the ubiquitin-proteasome system and immunoproteasome induction in response to oxidative stress occurs during X-ALD pathogenesis (Launay N et al., 2013, Brain 136, 891-904). Here, it was observed that temsirolimus treatment normalized chymotrypsin-like proteasome activity (FIG. 7E) and prevented the induction of the immunoproteasome subunits β1i/LMP2 and β5i/LMP7 (FIG. 7F).

Example 8: Temsirolimus Prevents Axonal Degeneration in Abcd1$^{-/-}$/Abcd2$^{-/-}$ Mice Abcd1−/−/Abcd2−/− mice have a neuropathological phenotype characterized by (i) increased labelling with 8-oxo-7,8-dihydro-2'-deoxyguanosine (8-oxodG), a marker of oxidative DNA damage, in motor neurons; (ii) microgliosis and astrocytosis, as revealed by Iba-1 and glial fibrillary acidic protein (GFAP) staining, respectively; (iii) axonal damage, as shown by the accumulation of amyloid precursor protein (APP) and synaptophysin in axonal swellings; and (iv) scattered myelin debris, evidenced by Sudan black staining {López-Erauskin J, et al., 2011, Ann Neurol 70, 84-92}.

Figure 8:
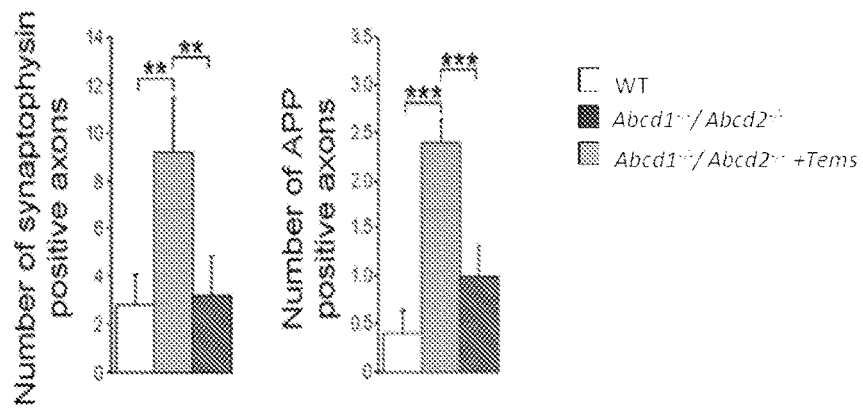
FIG. 8: Quantification of synaptophysin and APP accumulation in axonal swellings from WT, Abcd1−/−/Abcd2−/− and Abcd1−/−/Abcd2−/−+Tems mice. Data represent the mean±SD of 5-6 mice per genotype and condition. $p<0.01$ and *$p<0.001$.

As shown in FIG. 8, treatment of the Abcd1−/−/Abcd2−/− reduced the accumulation of markers of axonal damage (synaptophysin and APP) and DNA oxidation and the number of reactive astrocytes and reactive microglia to control levels (data not shown). Likewise, temsirolimus was able to improve motor neurons health in spinal cord from XALD mice.

Figure 9:
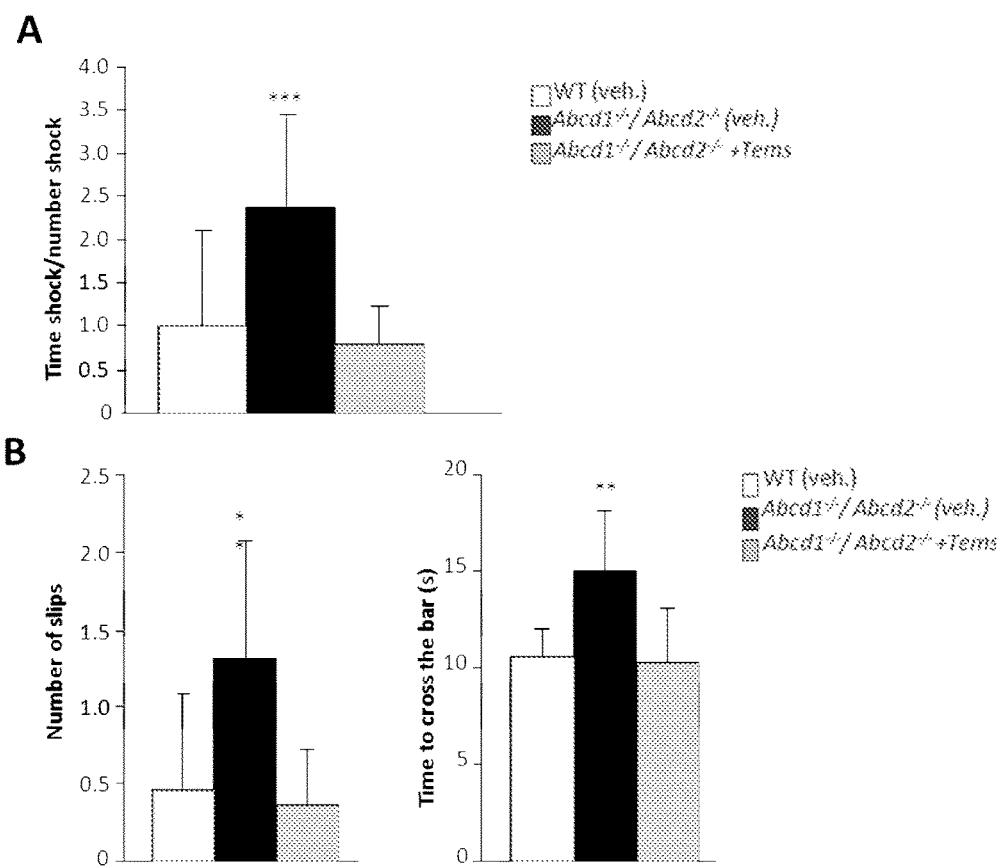
FIG. 9: Treadmill experiments (A) and Bar-cross tests (B) were carried out at 20 months of age with vehicle (veh.) treated WT or Abcd1−/−/Abcd2−/− mice or with temsirolimus treated (+Tems)Abcd1−/−/Abcd2−/− mice. $p<0.01$ and *$p<0.001$.

Example 9: Temsirolimus Halts the Progression of Locomotor Deficits in Abcd1$^{-/-}$/Abcd2$^{-/-}$ Mice Locomotor deficits in Abcd1−/−/Abcd2−/− mice were evaluated by treadmill and bar cross tests after temsirolimus treatment. In the treadmill test, the double knockout mice showed an increase in the ratio between the time length of the shocks and the number of shocks compared to wild type mice, reflecting a locomotor disability. Interestingly, temsirolimus treatment normalized this ratio (FIG. 9A).

In the bar cross experiments, double-knockout mutants often failed to maintain their balance, and they displayed a greater tendency to slip off the bar and longer time latencies in reaching the platform at the opposite end of the bar (López-Erauskin J, et al., 2011. Ann Neurol 70, 84-92). Following temsirolimus treatment, the number of slips and the time needed to cross the bar were normalized (FIG. 9B).

Overall, these data indicate that temsirolimus treatment stops the progression of locomotor deficits in X-ALD mice.

The invention claimed is:
1. A method for the treatment of X-Adrenoleukodystrophy (X-ALD) in a subject, said method comprising administering to a subject in need thereof a therapeutically effective amount of a specific mTOR inhibitor.

2. The method according to claim 1 wherein said specific mTOR inhibitor is a rapamycin-derivative.

3. The method according to claim 2 wherein said rapamycin derivative is temsirolimus.

4. The method according to claim 1 wherein the X-ALD is selected from adrenomyeloneuropathy (AMN), cerebral adrenomyeloneuropathy (cAMN) and childhood adrenoleukodystrophy (cALD).

5. A method for the treatment of X-Adrenoleukodystrophy (X-ALD) in a subject, said method comprising administering to a subject in need thereof a therapeutically effective amount of a composition, said composition comprising a specific mTOR inhibitor and a compound selected from the group consisting of an mTOR-independent autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hipolipidemic drug.

6. The method according to claim 5 wherein the X-ALD is selected from adrenomyeloneuropathy (AMN), cerebral adrenomyeloneuropathy (cAMN) and childhood adrenoleukodystrophy (cALD).

7. The method according to claim 5, wherein said specific mTOR inhibitor is a rapamycin-derivative.

8. The method according to claim 7, wherein said rapamycin-derivative is temsirolimus.

9. A method according to claim 1, wherein the mTOR inhibitor is administered in combination with a compound selected from the group consisting of an mTOR-independent autophagy inducer, an antioxidant, an antioxidant targeted to mitochondria, a histone deacetylase inhibitor, an inhibitor of mitochondria transition pore opening, an anti-inflammatory drug, a PPAR agonist, a RXR agonist, a sirtuin 1 agonist, and a hipolipidemic drug.

10. The method according to claim 9 wherein said mTOR independent autophagy inducer is selected from the group consisting of trehalose, ranitidine, spermidine, resveratrol, verapamil, loperamide, amidarone, trifluoperazine, monoxidil, 2'5'-dideoxyadenosine, tamoxifen, dimethylfumarate, thiazolinediones, 9-cis-retinoic acid, bexarotene, fluspirilene, trifluoperazine, penitrem A, pimozide, propranolol, vitamin E, α-lipoic acid, N-acetyl cysteine, lithium and combinations thereof.

* * * * *